(12) United States Patent
Sugawara

(10) Patent No.: US 7,551,282 B2
(45) Date of Patent: Jun. 23, 2009

(54) BODY FLUID CONSTITUENTS MEASUREMENT DEVICE

(75) Inventor: Yoshihisa Sugawara, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/195,604

(22) Filed: Aug. 21, 2008

(65) Prior Publication Data

US 2008/0309939 A1    Dec. 18, 2008

Related U.S. Application Data

(63) Continuation of application No. PCT/JP2007/056179, filed on Mar. 26, 2007.

(30) Foreign Application Priority Data

Mar. 28, 2006  (JP) ............................. 2006-088686

(51) Int. Cl.
*G01J 3/50* (2006.01)
*G01N 21/78* (2006.01)
*G01N 33/52* (2006.01)
(52) U.S. Cl. ........................................ 356/402; 356/39
(58) Field of Classification Search ............... 356/39, 356/402

See application file for complete search history.

(56) References Cited

FOREIGN PATENT DOCUMENTS

| JP | 2-259573 A | 10/1990 |
|---|---|---|
| JP | 3-073828 A | 3/1991 |
| JP | 3-095440 A | 4/1991 |
| JP | 10-318928 A | 12/1998 |
| JP | 2002-168862 A | 6/2002 |
| JP | 2005-172532 A | 6/2005 |

OTHER PUBLICATIONS

Form PCT/ISA/210 (International Search Report) dated Jun. 12, 2007.
Form PCT/ISA/237 (Written Opinion of the International Searching Authority) dated Jun. 12, 2007.
Norio Kashima et al., "Temperature Properties of a Super Luminosity LED", The Institute of Electronics, Information and Communication Engineers, Sogo Taikai Koen Ronbunshu, Mar. 3, 2003, p. 525 (cited in the attached International Search Report and Written Opinion).
Masanori Hayashi et al., "LED Driver for the Smoke Detector", The Institute of Electrical Engineers of Japan, Oct. 24, 1996, vol. ECT-96, No. 57-66, pp. 11-14, Matsushita Electric Works, Ltd., Kadoma, Osaka, Japan (cited in the attached International Search Report and Written Opinion).

*Primary Examiner*—F. L Evans
(74) *Attorney, Agent, or Firm*—Buchanan Ingersoll & Rooney PC

(57) ABSTRACT

A body fluid constituents measurement device, which performs measurement under a setting where light intensity of the light-emitting element is suitably stabilized, is provided. The present invention is a body fluid constituents measurement device which comprises: a light-emitting element that emits light onto a test paper onto which body fluid is spotted, a light receiving element which receives reflected light of the light emitted by said light-emitting element, a temperature measurement unit which measures the ambient temperature in the vicinity of said light-emitting element, a determination unit which determines conditions of light emission based on said temperature measured at said temperature measurement unit in order to stabilize light intensity of said light-emitting element, and a driving control unit which controls driving of said light-emitting element based on the conditions of light emission; and is characterized in that it starts measurement of body fluid constituents after the light intensity of light emitted by said light-emitting element has been stabilized.

16 Claims, 39 Drawing Sheets

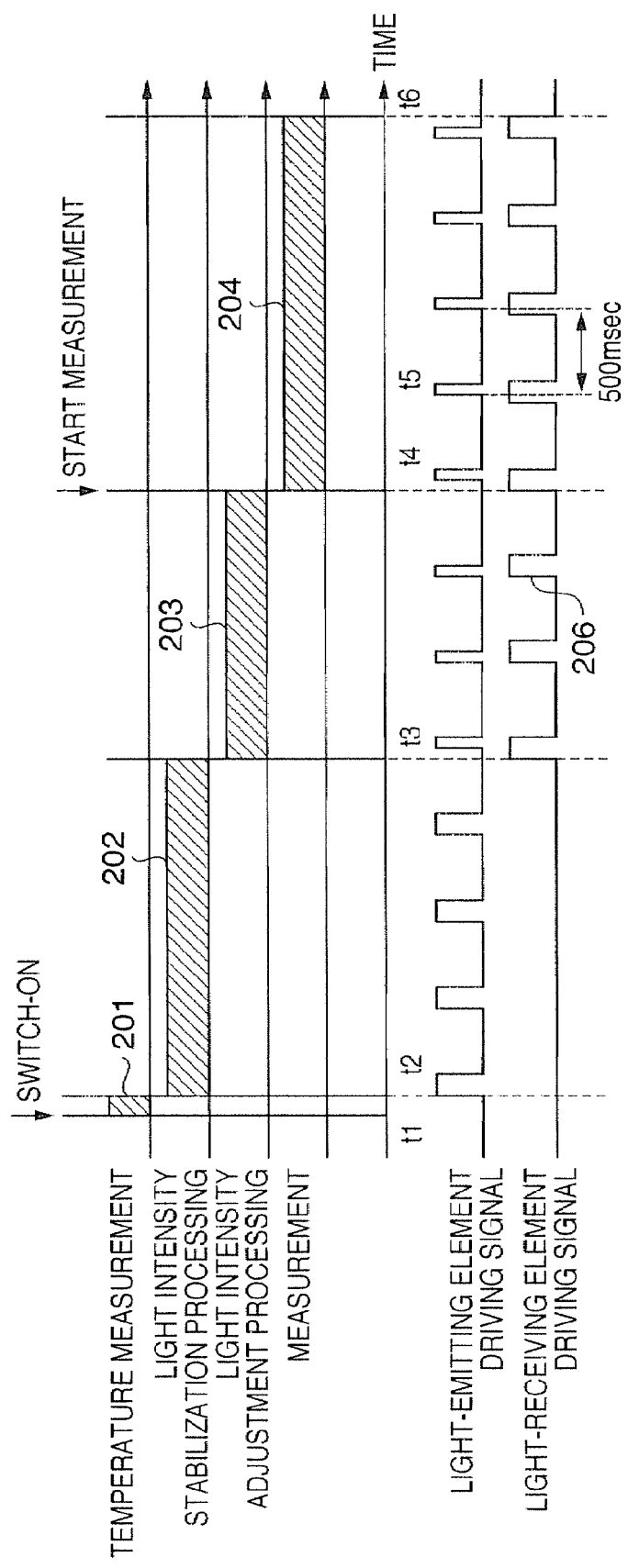

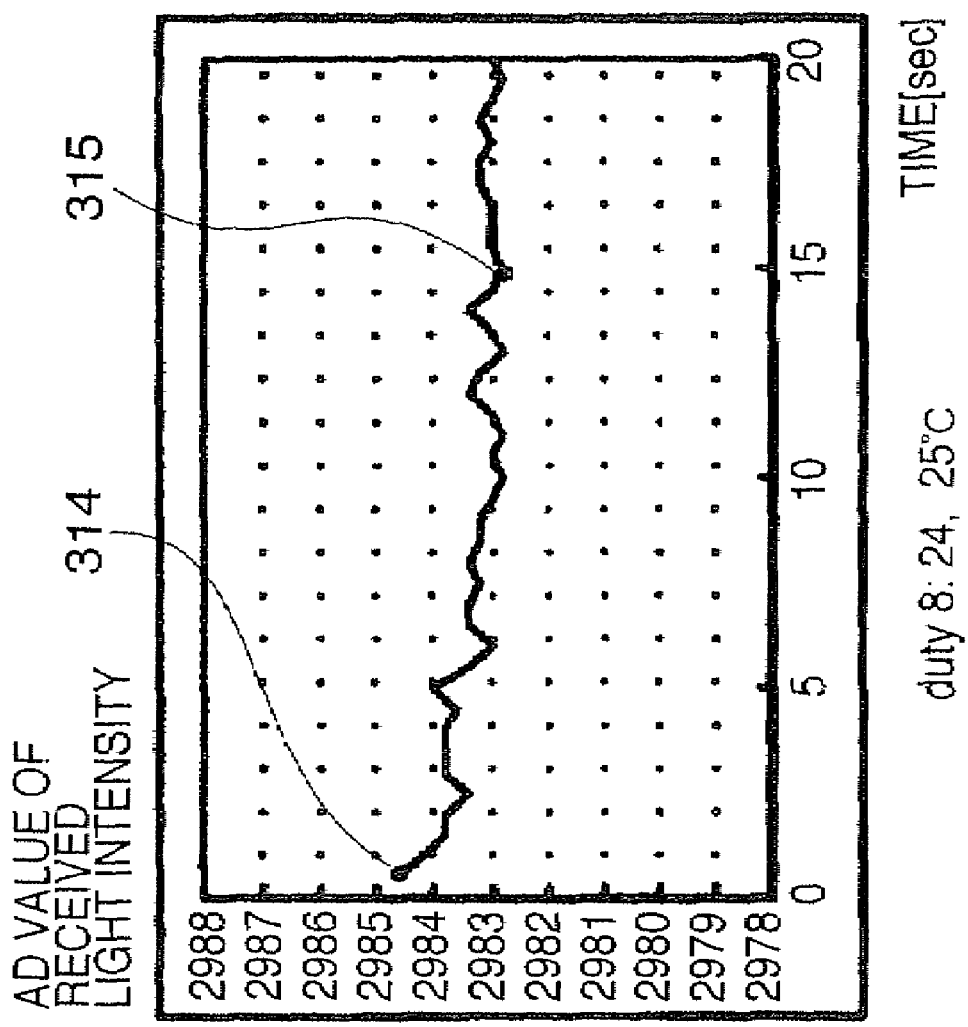

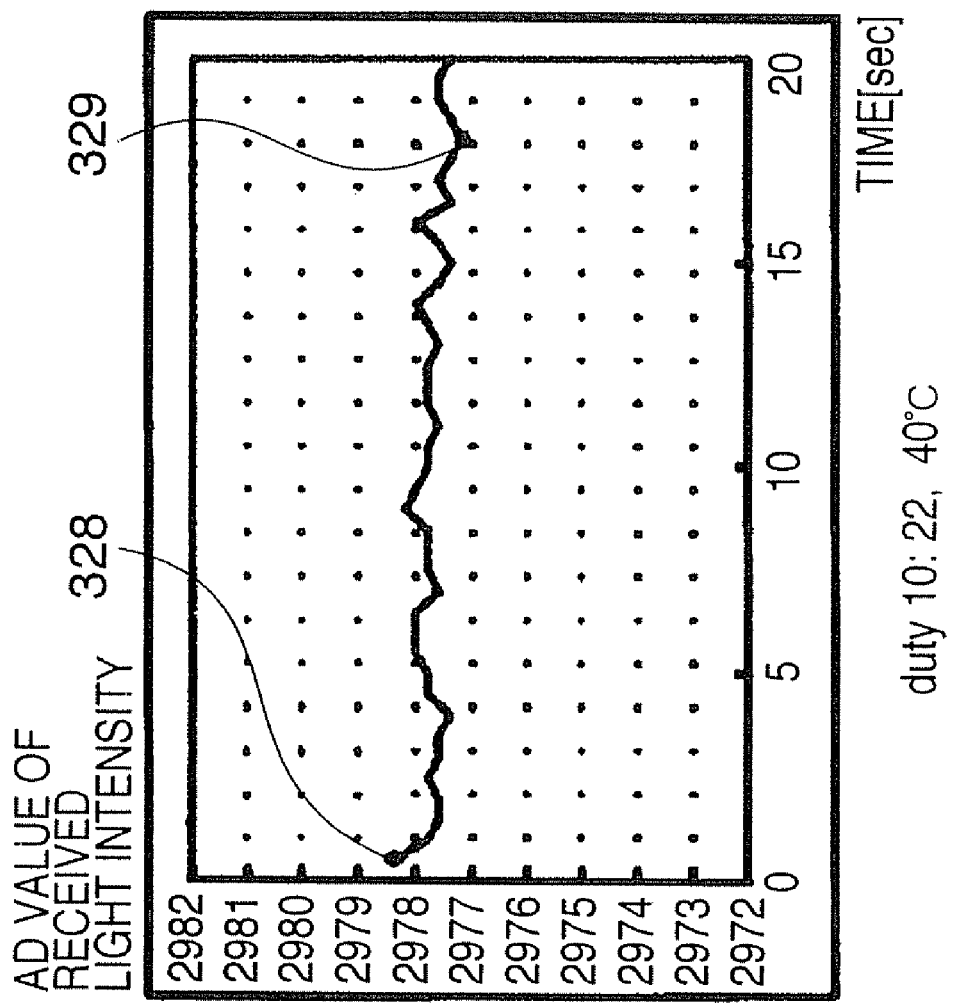
F I G. 3I

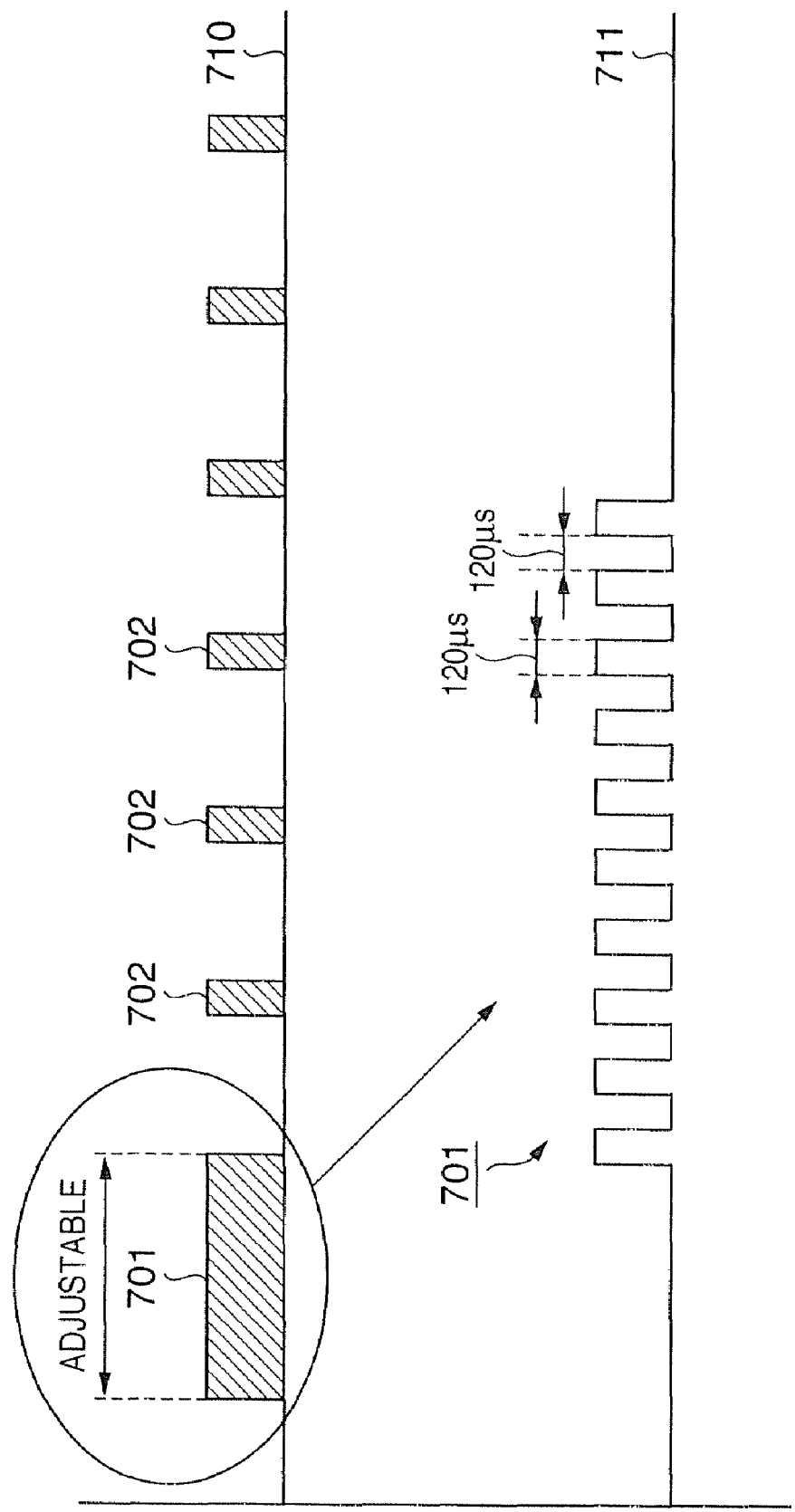

FIG. 11

| TEMPERATURE [°C] | 5.0 LESS THAN | 5.1~10.0 | 10.1~15.0 | 15.1~20.0 | 20.1~25.0 | 25.1~30.0 | 30.1~35.0 | 35.1 MORE THAN |
|---|---|---|---|---|---|---|---|---|
| DRIVING TIME [sec] | 0.64 | 0.65 | 0.66 | 0.66 | 0.67 | 0.68 | 0.70 | 0.71 |

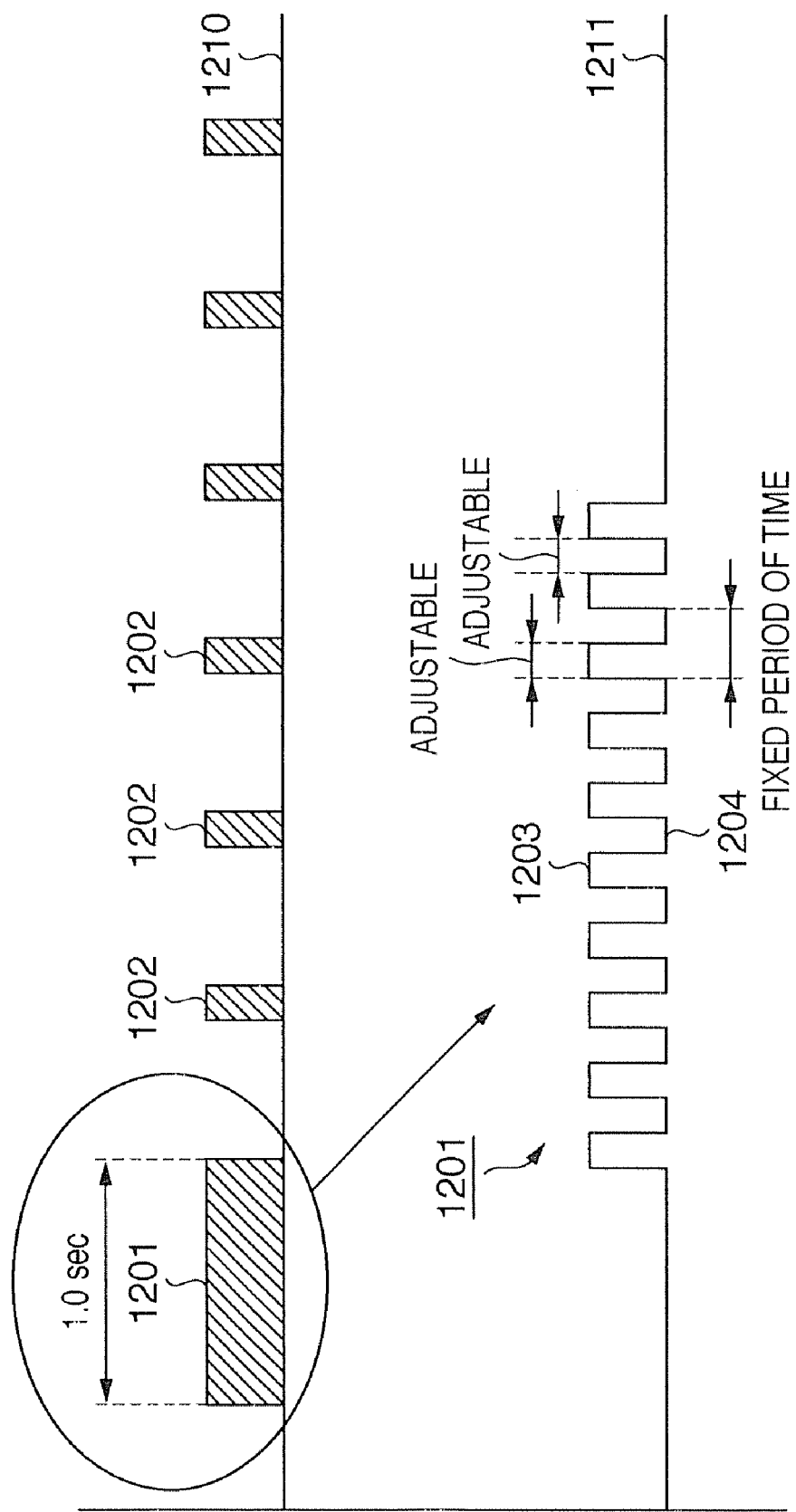

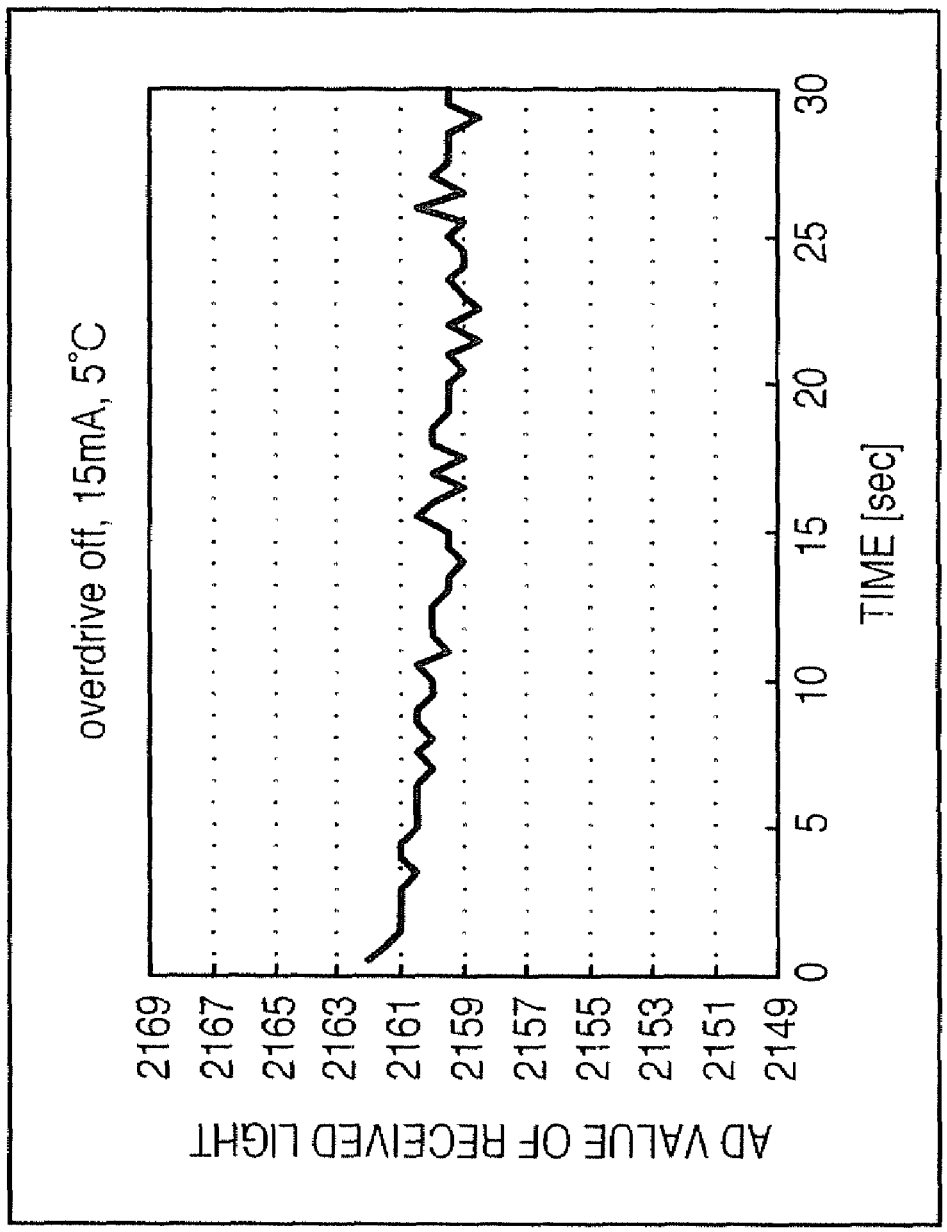
F I G. 15A

FIG. 16

| TEMPERATURE [°C] | 5.0 LESS THAN | 5.1~10.0 | 10.1~15.0 | 15.1~20.0 | 20.1~25.0 | 25.1~30.0 | 30.1~35.0 | 35.1 MORE THAN |
|---|---|---|---|---|---|---|---|---|
| DUTY RATIO | 1:1.61 | 1:1.60 | 1:1.59 | 1:1.57 | 1:1.56 | 1:1.51 | 1:1.47 | 1:1.42 |

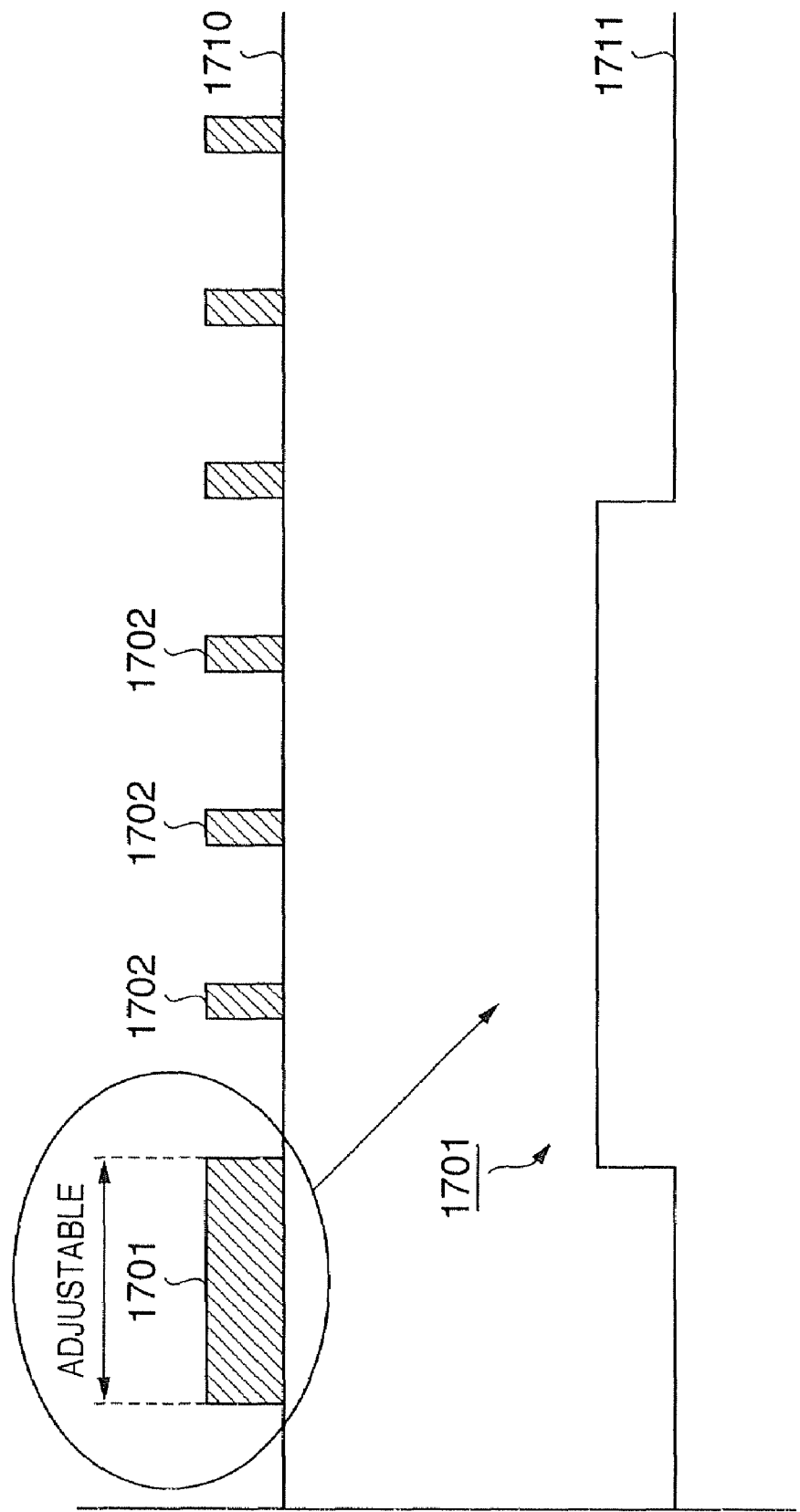

F I G. 21

| TEMPERATURE [°C] | 5.0 LESS THAN | 5.1~10.0 | 10.1~15.0 | 15.1~20.0 | 20.1~25.0 | 25.1~30.0 | 30.1~35.0 | 35.1 MORE THAN |
|---|---|---|---|---|---|---|---|---|
| CONTINUOUS DRIVING TIME [ms] | 225 | 228 | 230 | 233 | 235 | 240 | 246 | 251 |

BODY FLUID CONSTITUENTS MEASUREMENT DEVICE

TECHNICAL FIELD

The current invention relates to a body fluid constituents measurement device which measures constituents of body fluids. In particular, the current invention relates to a body fluid constituents measurement device having an optical sensor.

BACKGROUND ART

Among devices that measure constituents of body fluids, those that measure constituents of blood are known. Such body fluid constituents measurement devices are used for purposes such as measurement of the blood sugar levels of patients with diabetes. Such body fluid constituents measurement devices are equipped with test paper which changes color when reacted with blood glucose, blood is applied to the test paper, and the change in color is optically measured by means of colorimetry for quantification of the blood glucose level.

In such blood glucose measurement devices, the blood glucose level is determined by measuring the change in color of the test paper onto which blood is spotted. Further, as the method of measurement, a light-emitting element such as an LED is used to illuminate the test paper, and the intensity of the reflected light is detected using a light-receiving element such as a light receiving diode.

However, light intensity emitted by light-emitting elements such as an LED can decrease due to generation of heat during light emission. The loss in light intensity of an LED is especially large right after power activation (i.e., turning on the LED). Further, the blood sugar level is calculated by comparing the measurement data prior to spotting blood with the measurement data in the state that chemical reaction stablizes after spotting blood. Accordingly, decrease in the light intensity of an LED during measurement leads to problems in accuracy of measurement data. In order to stabilize light intensity during measurements, it is necessary to carry out light intensity stabilization processing prior to measurements after the device is switched on. The patent reference 1 shows a technique that measurements of reflected light is made after the light intensity emitted from the light source has stabilized.

Patent reference 2 discloses a body fluid constituents measurement device in which the light-emitting element is pulse-driven in bursts at intervals, and the average of reflected light intensities from a plurality of pulse signals are obtained for calculating measurement values such as blood glucose level. The body fluid constituents measurement device of patent reference 2 initiates measurement after a predetermined period of time has passed since switching on the light-emitting element, and averages the light intensities of reflected light during each burst, thereby improving accuracy. Further, the body fluid constituents measurement device of patent reference 2 shortens measurement time by initiating measurement prior to stabilization of the emission condition of the light-emitting element.

Patent reference 3 discloses a body fluid constituents measurement device which is easy to operate and is highly accurate. The body fluid constituents measurement device of patented reference 3 quantifies constituents by obtaining differences between the intensities of reflected light measured when pulsed light is not emitted and when pulsed light is emitted. Further, the body fluid constituents measurement device of patent reference 3 improves accuracy of the measurement result by measuring the light pulsed at a interval which is half cycle of the commercial alternating current or its integral multiples when measuring the difference in intensities of the reflected light.

Patent reference 1: Japanese Patent Laid-open No. H03-73828

Patent reference 2: Japanese Patent Laid-open No. 2002-168862

Patent reference 3: Japanese Patent Laid-open No. H10-318928

DISCLOSURE OF THE INVENTION

Problems that the Invention is to Solve

However, body fluid constituents measurement devices such as the one in patent reference 1 have a problem in that they require a long time for stabilization of light intensity prior to making measurements. On the other hand, the body fluid constituents measurement device of patent reference 2 shortens measurement time by initiating measurement prior to stabilization of light intensity. However, its accuracy is not on par with methods that measurements are carried out after stabilization of light intensity. Further, the body fluid constituents measurement device of patent reference 3 does not touch upon the issue of light intensity stabilization after switching on the device.

Accordingly, in order to solve above-mentioned problems, the present invention provides a body fluid constituents measurement device which efficiently stabilizes emitted light intensity after being switched on, leading to early start of measurement of body fluid constituents.

Means of Solving the Problems

In order to solve the above-mentioned problem, the present invention according to one of the embodiments is a body fluid constituents measurement device which utilizes a test paper holding a coloring reagent which reacts to a predetermined constituent of body fluid and optically measures a quantity of the predetermined constituent by means of colorimetry, characterized in that it comprises: a light-emitting element configured to emit irradiating light to said test paper, a light-receiving element configured to receive reflected light from said test paper, a driving control unit configured to control driving of said light-emitting element, a temperature measurement unit configured to measure ambient temperature in the vicinity of said light-emitting element, and a determination unit configured to determine a first light emission condition for driving said light-emitting element prior to performing measurements of a quantity of the predetermined constituent based on the ambient temperature measured by said temperature measurement unit, wherein after said light-emitting element is driven for a predetermined period of time under said first light emission condition, the body fluid is provided to said test paper under a second light emission condition different from the first light emission condition, and the measurement of the quantity of the predetermined constituent of the body fluid is performed by detecting at said light-receiving element a reflected light intensity from the test paper where color change occurs according to the quantity of the predetermined constituent of the body fluid.

EFFECTS OF THE INVENTION

According to the present invention, it is possible to efficiently stabilize light intensity of emitted light and early measure constituents of body fluids. Further, as stabilization of light intensity is performed on the basis of the ambient temperature, it is possible to avoid excessive driving of the light-emitting element and to reduce power consumption.

Other features and advantages of the current invention will be clear from the following explanation referring to the attached figures. In regard to the attached figures, same reference numerals are used for the components which are essentially the same.

BRIEF DESCRIPTION OF DRAWINGS

The attached figures are included in and comprise a part of the specification. The figures represent the embodiments of the present invention and are used for explaining implementation and the principles of the present invention with the specification.

FIG. 2A is a diagram showing the process flow until measurement according to the present invention.

FIGS. 3D to 3F show the measurement results by the light receiving element when the pulse width (length) at the light emitting element is altered according to different environmental temperatures.

FIGS. 3G to 3I show the measurement results by the light receiving element when the pulse width (length) at the light emitting element is altered according to different environmental temperatures.

FIG. 7 shows an exemplary driving pulse of the light-emitting element 114 during measurement of a body fluid constituent according to the first embodiment of the present invention.

FIG. 11 shows a table 1100 which records light emission conditions for stabilization processing of the first embodiment.

FIG. 12 shows an exemplary driving pulse of the light-emitting element 114 during measurement of a body fluid constituent according to a second embodiment of the present invention.

FIGS. 15A and 15B show the measurement results of the received light intensity according to the second embodiment.

FIG. 16 shows a table 1600 which records light emission conditions for stabilization processing of the second embodiment.

FIG. 17 shows an exemplary driving pulse of light-emitting element 114 during measurement of a body fluid constituent according to a third embodiment of the present invention.

FIG. 21 shows a table 2100 which records light emission conditions for stabilization processing of the third embodiment.

BEST MODE FOR CARRYING OUT THE INVENTION

Figure 1:
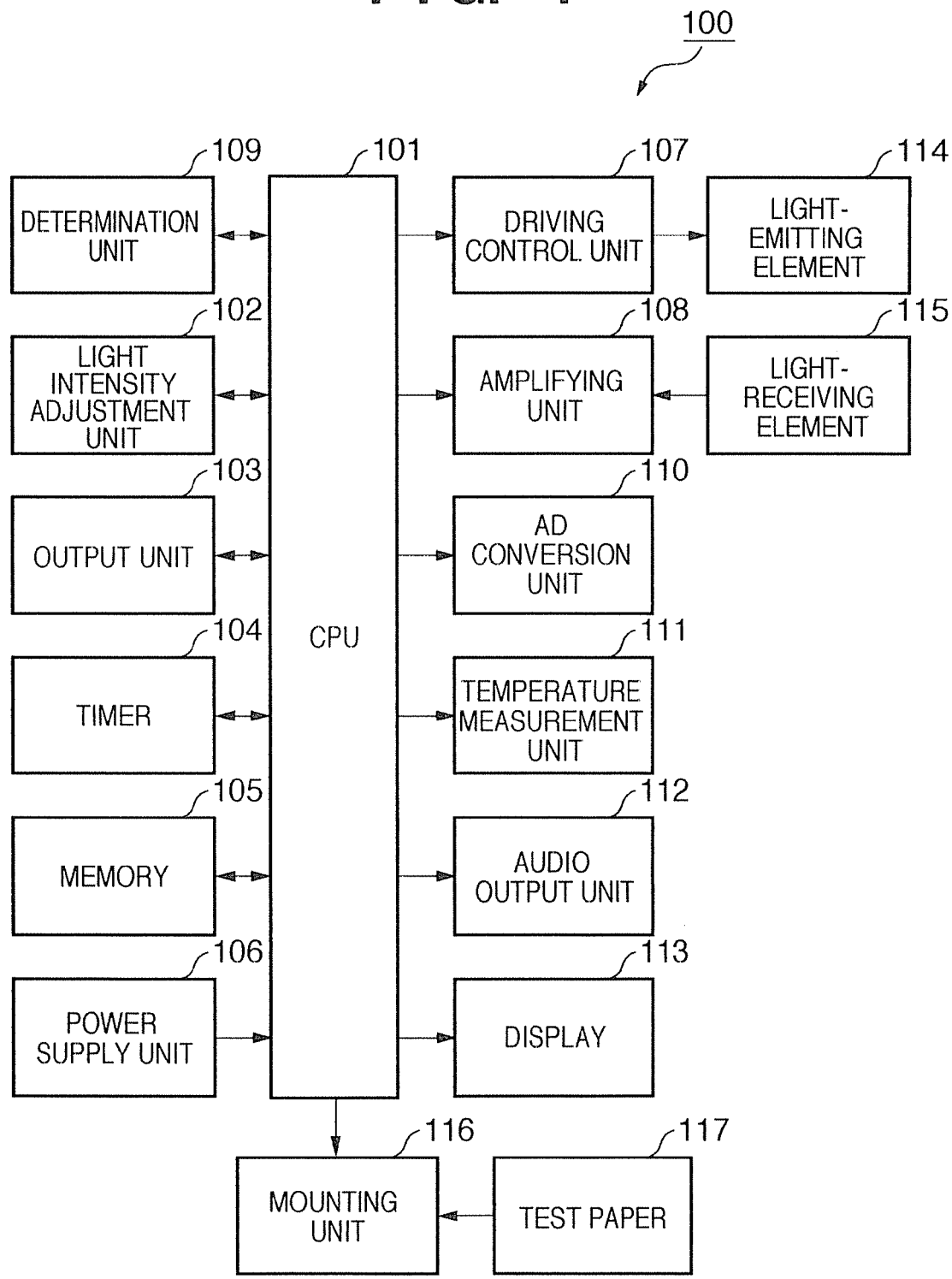
FIG. 1 is a block diagram showing an exemplary structure of the body fluid constituents measurement device of the present invention.

FIG. 1 is a block diagram showing an exemplary structure of the body fluid constituents measurement device of the present invention. However, the structure of this body fluid constituents measurement device is given only as an example, and does not limit the structure of body fluid constituents measurement device of the present invention in any way. The structure of the body fluid constituents measurement device will be explained only in regard to its elements which are essential for explanation of the current invention.

A body fluid constituents measurement device 100 comprises a CPU 101 which controls each of the components. The body fluid constituents measurement device 100 comprises, as components functionally connected to the CPU 101, a determination unit 109, a light intensity adjustment unit 102, an output unit 103, a driving control unit 107, a light-emitting element 114, an amplifying unit 108, a light receiving element 115, an AD conversion unit 110, a temperature measurement unit 111 and a mounting unit 116. The mounting unit 116 during measurements is mounted with test paper 117 holding a coloring reagent. Further, application of the specimen (for example, blood) to the test paper 117 is done by piercing the finger tip, the earlobe or the like with a needle, a scalpel or the like, and either directly applying a small amount of blood which has bled out to the surface of the skin or adsorbing via a small opening which is formed on the mounting unit 116.

The light-emitting element 114 is comprised of an LED, etc., and illuminates light onto the test paper 117 onto which body fluid is spotted. Additionally, the light-receiving element 115 is comprised of a light-receiving diode, etc., and converts the light emitted by the light-emitting element 114 and reflected by the test paper to electric signals. Further, energy of the converted electric signal is amplified by the amplifying unit 108, and the amplified electric signal is inputted to the AD conversion unit 110. The AD conversion unit 110 converts inputted analog signals to digital signals.

The temperature measurement unit 111 includes a temperature sensor which is placed in the vicinity of the light-emitting element 114, and measures the ambient temperature in the vicinity of the light-emitting element 114. The determination unit 109 determines conditions of light emission in order to stabilize light intensity emitted by the light-emitting element 114 based on the ambient temperature measured by the temperature measurement unit 111. The conditions of light emission in this context refer to various parameters concerning emission of light such as pulse width, pulse amplitude, or pulse period. The driving control unit 107 is connected with the light-emitting element 114, and controls driving of the light-emitting element according to the conditions of light emission determined by the determination unit 109. From here on, a set of processing which controls the driving of the light-emitting element 114 according to the conditions of light emission determined by measurement of the ambient temperature prior to measurement of body fluid constituents will be referred to as "light intensity stabilization processing". The light intensity stabilization processing is required for improving accuracy of the measurement results by stabilizing the light emitted by the light-emitting element prior to making measurements of the body fluid constituents. The term "stabilization" in this context refers to convergence of fluctuation in emitted light intensity.

Further, the light intensity adjustment unit 102 adjusts light intensity of measurement light based on the measured temperature of the surrounding. This processing is necessary in order to maintain a constant set of conditions at the time of measurement, which adjusts light intensity by tweaking the electric power supply required for light emission according to the ambient temperature of the surrounding. When light intensity is adjusted, the body fluid constituents measurement device 100 initiates measurement processing, with a fixed interval such as 500 msec in between each measurement. During measurement processing, it is possible to set the duty ratio (ON/OFF ratio) of the driving signal for the light-emitting element as, for example 4:28. Further, it can also be arranged to have the measurement results obtained from the measurement processing sent to external devices such as a host computer via an output unit 103.

Further, the present body fluid constituents measurement device 100 comprises a timer 104, a memory 105, an electric power supply unit 106, an audio output unit 112 and a display unit 113. The timer 104 can be utilized for measurements of light emission time and light emission intervals during light intensity stabilization processing, and also for measurements of light emission time and light emission intervals during measurement processing. The memory 105 comprises RAM, ROM, etc. Conditions of light emission, such as at least one of pulse width, pulse amplitude and pulse period (the number of pulses in a given period) for light emission of the light-emitting element 114 under the measured temperature of the surrounding, can be stored in the ROM. The electric power supply unit 106 supplies electric power to the body fluid constituents measurement device 100. The audio output unit 112 and the display unit 113 are utilized for purposes such as to output measurement results, and to report errors that occur during measurement to the user.

For measurement of blood sugar levels in the measurement processing, the method of performing colorimetric measurements before and after spotting blood onto the test paper and calculating the blood sugar level from the difference in the two colorimetric measurements is generally used. During this process, if the light intensity of emitted light from the light-emitting element 114 is not constantly maintained before and after spotting blood onto the test paper, accuracy of measurement results cannot be guaranteed. In order to guarantee the accuracy of measurement results, it is necessary to constantly maintain the light intensity of the light-emitting element 114 before and after adsorbing blood to the test paper.

Further, the body fluid constituents measurement device 100 is generally switched on just before the user carries out a measurement processing, and is expected to be usable immediately after being switched on. However, the device typically remains switched off when not being used, and immediately after being switched on, the temperature of the light-emitting element 114 is therefore the same as the ambient temperature. On top of this, during the process from turning on the device to rising temperature in itself by light-emitting and stabilization of the temperature of the light-emitting element 114, light intensity gradually declines leading to fluctuations, which makes it difficult to guarantee accurate measurement results from measurement processing during this period.

In order to address this, it is possible to converge declining light intensity and fluctuations by letting the light-emitting element 114 emit light for a predetermined period of time prior to measurements. However, this light intensity stabilization processing conventionally has required several tens of seconds because the light-emitting element 114 was driven under conditions which was identical to that of measurement processing (for example a duty ratio of ON:OFF=4:28). A user who wants to use the body fluid constituents measurement device 100 immediately after switching it on would feel that such a waiting period is extremely long.

In order to minimize the time needed for light intensity stabilization processing, the body fluid constituents measurement device 100 of the present invention measures the ambient temperature in the vicinity of the light emitting-element 114, determines conditions of light emission according to this measured temperature at the determination unit 109, and drives the light-emitting element 114 according to the determined conditions of light emission. The conditions of light emission determined here is different from the conditions of light emission for measurement processing, and favorable conditions for minimizing the time required for light intensity stabilization processing are set.

FIG. 2A is a timing chart showing the process flow from the start of power supply until measurement processing according to the present invention.

In the body fluid constituents measurement device 100, when electric power is supplied at a time point of t1, a temperature measurement processing 201 which measures the temperature of the surrounding with the temperature measurement unit 111 is performed. When the temperature of the surrounding is measured, the body fluid constituents measurement device 100 determines, at the determination unit 109, various conditions for light emission such as pulse width, pulse amplitude and pulse period for driving the light-emitting element 114 according to the temperature of the surrounding.

Subsequently, the body fluid constituents measurement device 100, at a time point t2, supplies driving signal 205 from the driving control unit 107 to the light-emitting element 114 according to the determined conditions of light emission, and performs light intensity stabilization processing 202 for a predetermined period of time. The time required for the light intensity stabilization processing 202 according to the present invention (:Tst=t3-t2) is to be approximately 0.3 to 2.0 seconds (preferably, 0.5 to 1.0 second).

It is well-known as general characteristics that the intensity of light emitted by typical light-emitting elements 114, such as an LED, drop when the temperature of the surrounding rises. Further, when compared under equal conditions, the higher the temperature of the surrounding is, the longer it takes for stabilization of light emitting behavior of the light-emitting element 114. The light intensity stabilization processing 202 of the present invention adjusts the conditions of light emission by setting the patterns of the driving signals 205 supplied to the light-emitting element 114 according to the temperature of the surrounding, stabilizes the light intensity of emitted light within a short period of time, and early enables to perform a constituent measurement processing.

Figure 2B:
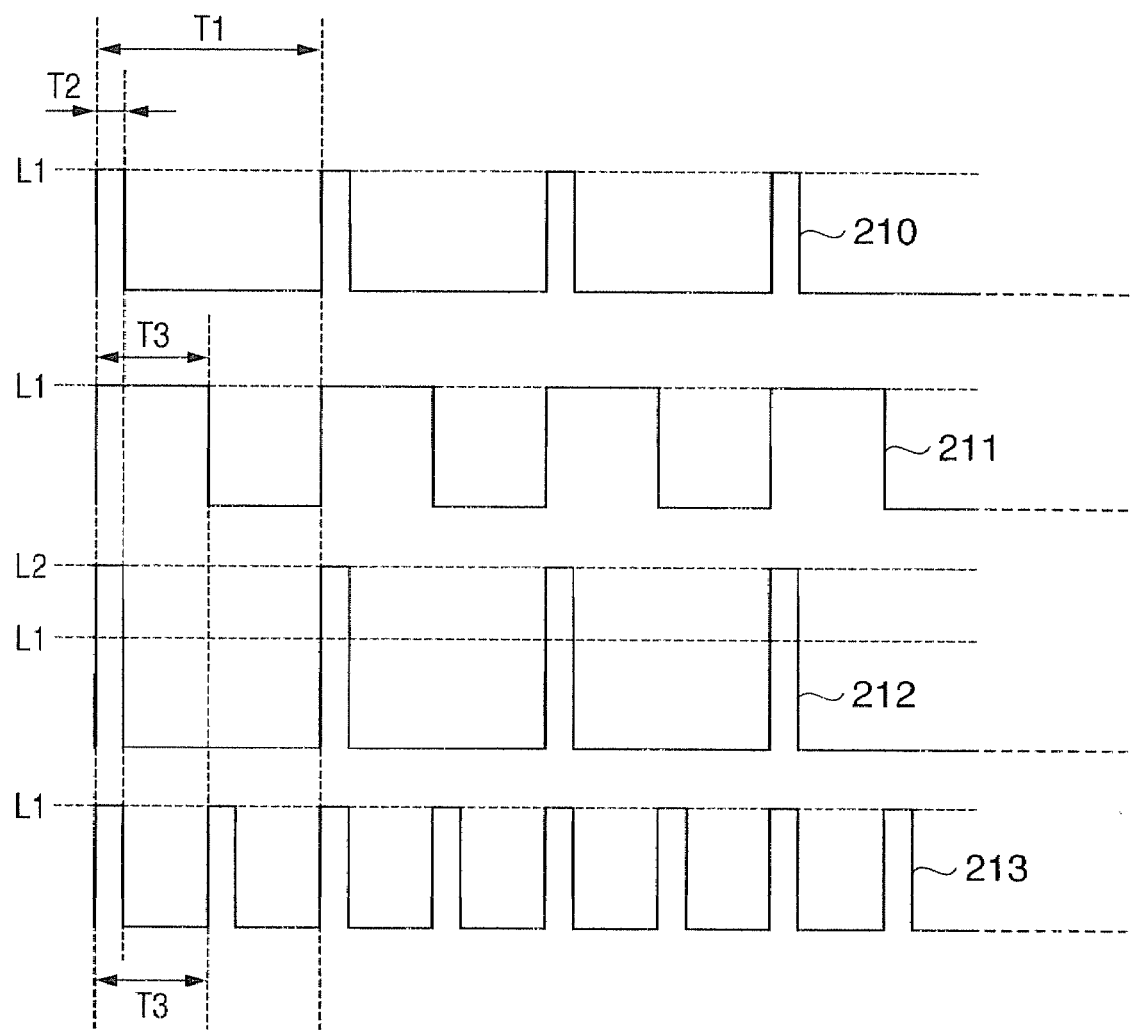
FIG. 2B is a diagram showing the pattern of the driving signal applied to a light-emitting element 114 during a light intensity stabilization process.

In further detail, as illustrated in FIG. 2B, by using driving signals with a larger pulse width (211), a higher pulse amplitude (212) or a shorter pulse period (213) than the driving signal 210 of the light-emitting element 114 used during measurement processing at a time point t4, it is possible to quickly move the light-emitting element 114 to the stabilized state, by exerting a heavy load on the light-emitting element 114 just after being switched on.

In 210 of FIG. 2B, an example of the waveform of the driving signal applied to a light-emitting element 114 during a measurement processing performed at the time point t4 in FIG. 2A is shown. At this time, if the pulse period and pulse width (the period in which the driving signal is high (or ON)) are set as T1 and T2, respectively, it is possible to express the duty ratio as T2:T1-T2. Further, the amplitude of the driving signal 210 is set as L1.

In contrast, 211 shows a waveform pattern of the driving signal where the pulse width of the driving signal applied to the light-emitting element 114 during the light intensity stabilizing processing 202 is set larger than that of the driving signal 210. In the driving signal 211, while the pulse period and pulse amplitude coincide with T1 and L1, respectively, by setting the pulse width as T3, the relationship between T3 and T2 becomes: T3>T2. In other words, the pulse width of the driving signal 211 is larger than the pulse width of the driving signal 210.

Next, 212 illustrates a waveform pattern of an driving signal in which the pulse amplitude of the driving signal applied to the light-emitting element 114 during the light intensity stabilizing processing 202 is set to be higher than that of the driving signal 210. In the driving signal 212, while the pulse period and pulse width coincide with T1 and T2 respectively, by setting the pulse amplitude as L2, the relationship between L2 and L1 becomes: L2>L1. In other words, the pulse amplitude of the driving signal 212 becomes higher than the pulse amplitude of the driving signal 210.

Further, 213 illustrates a waveform pattern of an driving signal in which the pulse period of the driving signal applied to the light-emitting element 114 during light stabilizing processing 202 is set to be shorter than that of the driving signal 210. In the driving signal 213, while the pulse width and pulse amplitude coincide with T2 and L1 respectively, by setting the pulse period as T3, the relationship between T1 and T3 becomes: T1>T3. In other words, the pulse period of the driving signal 213 becomes shorter than the pulse period of the driving signal 210.

When the ambient temperature is low, stabilization of light intensity is much easier in comparison to when the ambient temperature is high. Therefore, the light intensity stabilization processing of the present invention can suppress electricity consumption needed for light intensity stabilization processing by, for example shortening the pulse width.

Following stabilization of light emitted by the light-emitting element 114 by above-mentioned light intensity stabilization processing, the body fluid constituents measurement device 100 performs light intensity adjustment processing in order to adjust light intensity during measurement using the light intensity adjustment unit 102 at a time point t3 based on the measured ambient temperature. At this point, the body fluid constituents measurement device 100 simultaneously performs driving of the light-receiving element 115 in order to receive reflected light of the light emitted by the light-emitting element 114. The light-receiving element 115, as shown in FIG. 2A, is driven according to the driving of the light-emitting element 114, and is driven slightly longer than the driving of the light-emitting element 114 with margins before and after. Accordingly, the light-receiving element 115 according to the present invention is not driven until the time point t3. By this setup, it is possible to lengthen the operating life-span of the light-receiving element 115, and lower the consumption of electricity for the light intensity stabilization processing.

These processing steps up to the light intensity adjustment processing are preprocessing (preparatory) steps. According to the present invention, the time (t1 to t4) required for the preprocessing steps is approximately 5 seconds. Subsequently, at the time point t4, the body fluid constituents measurement device 100 initiates measurement by driving the light-emitting element 114 according to the predetermined duty ratio at such as 500 msec intervals, as shown in FIG. 2A.

Figure 3A:
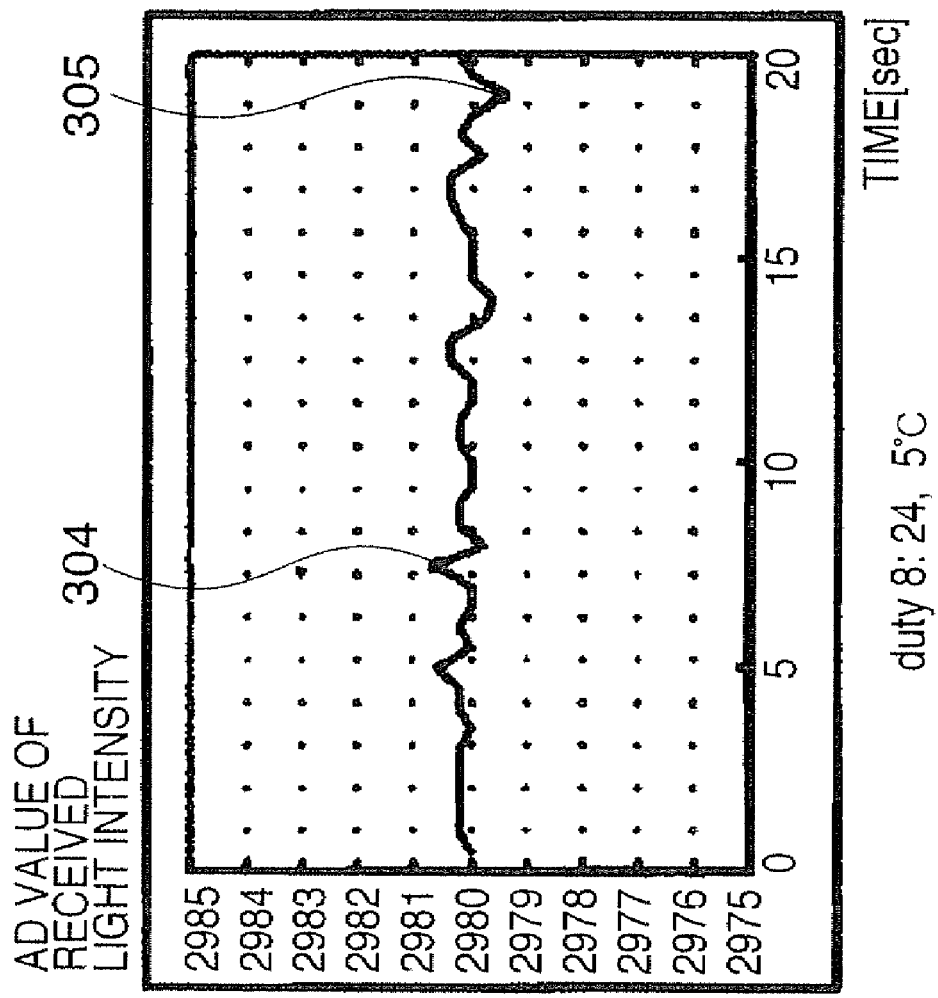
FIGS. 3A to 3C show the measurement results by the light receiving element when the pulse width (length) at the light emitting element is altered according to different environmental temperatures.
Figure 3B:
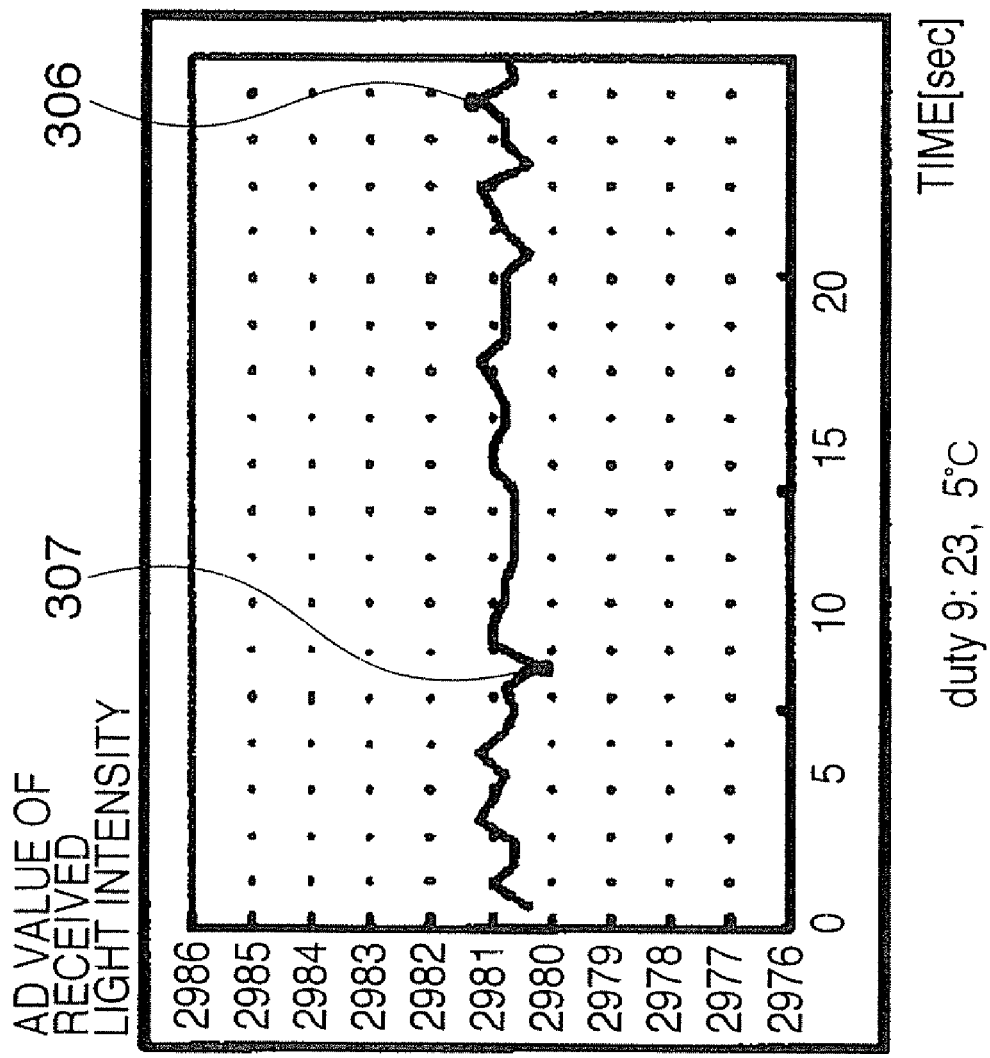
Figure 3C:
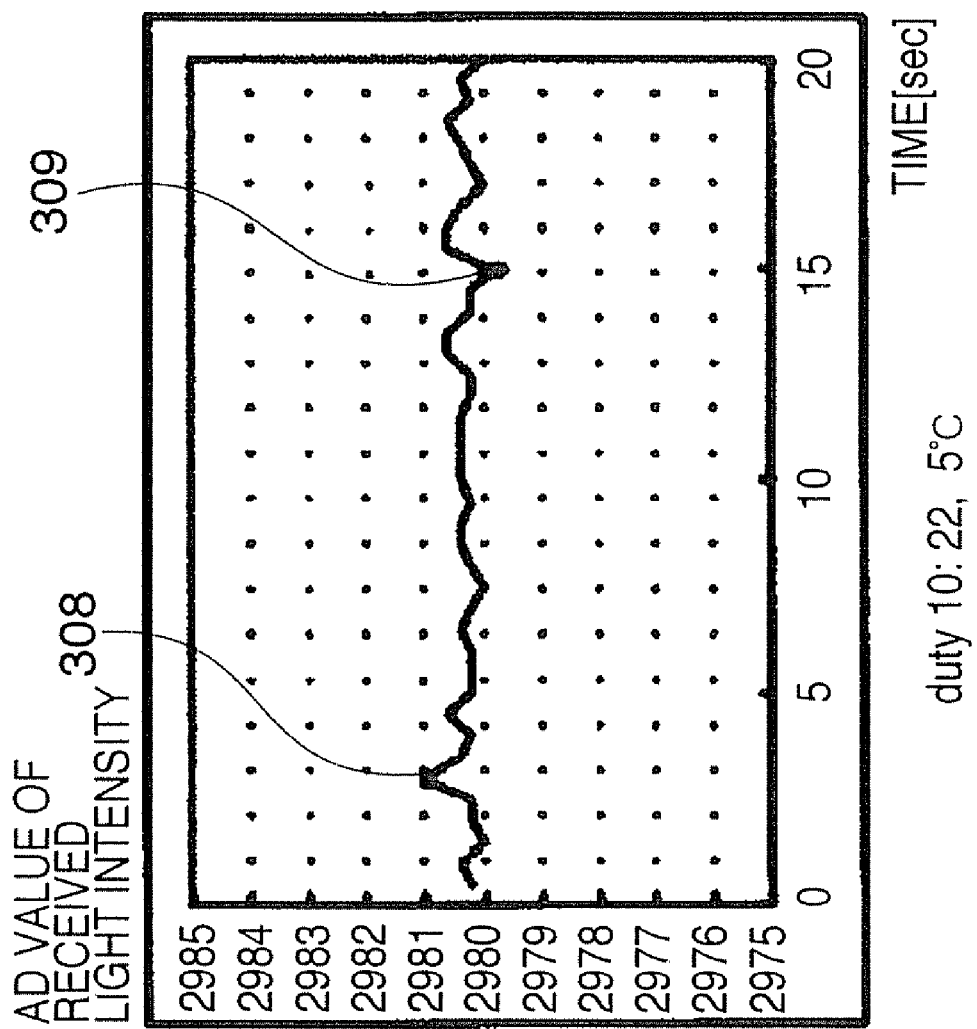
Figure 3E:
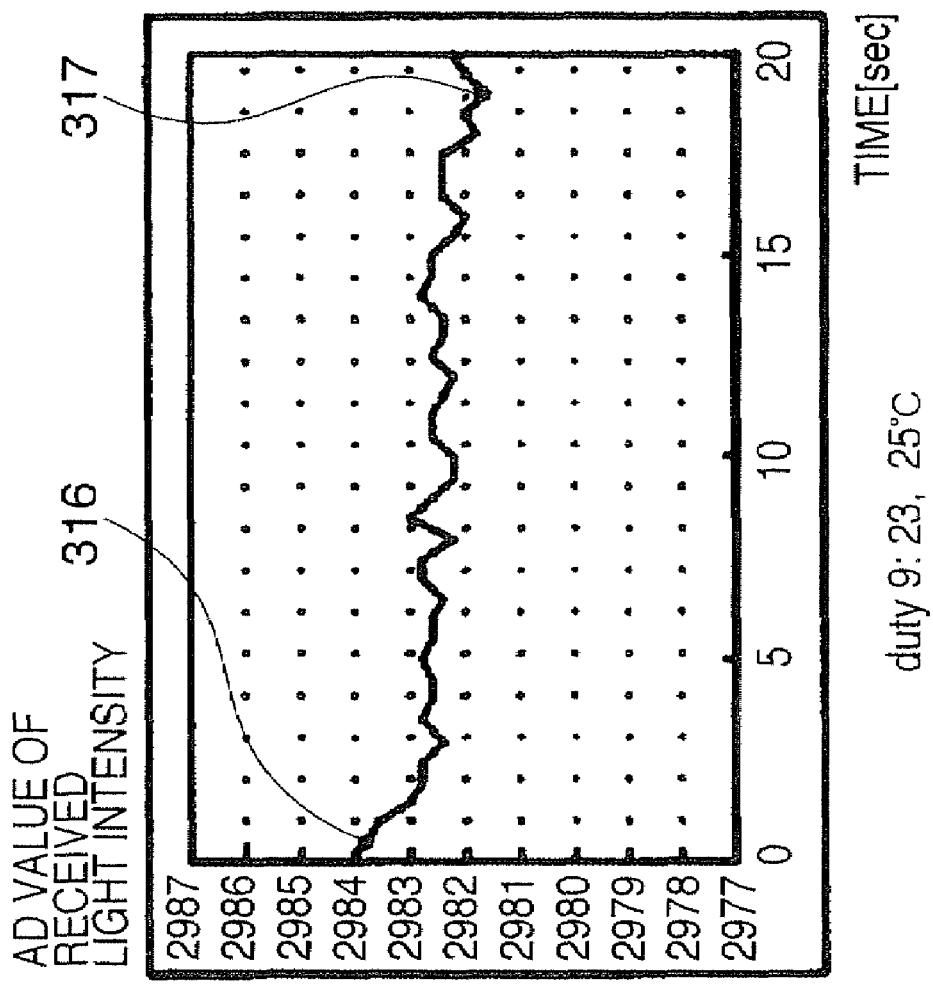
Figure 3F:
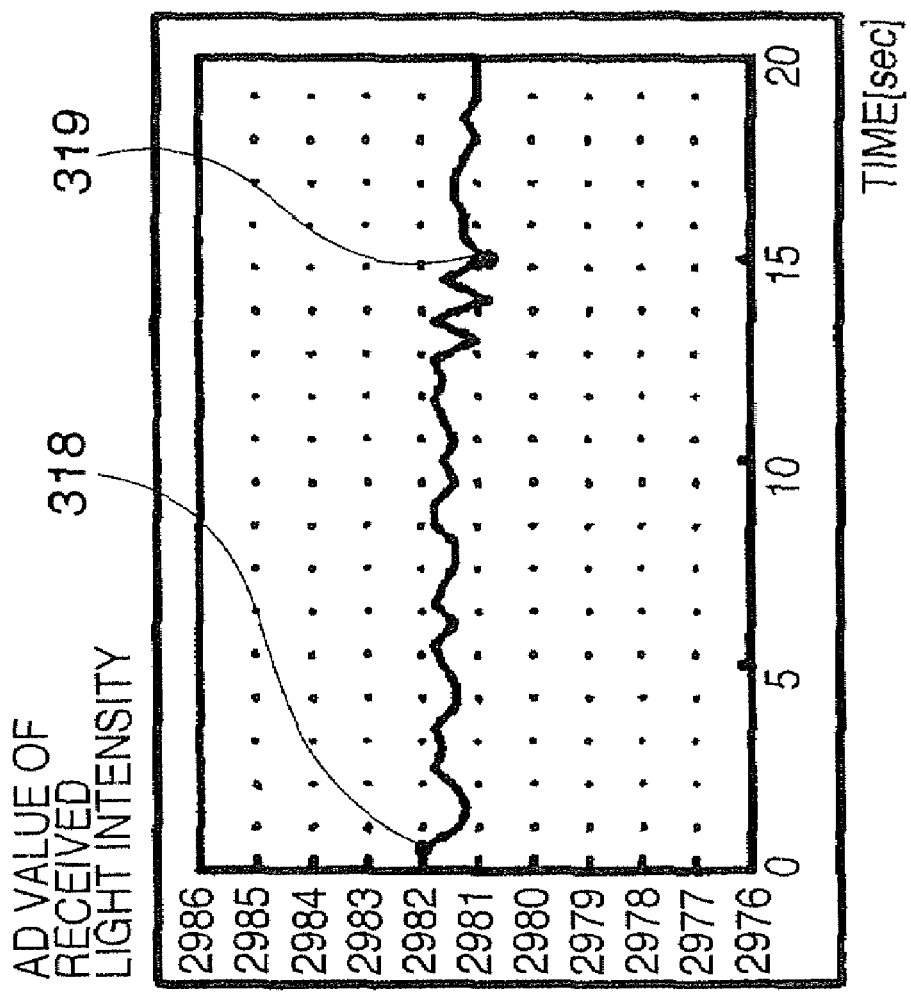
Figure 3G:
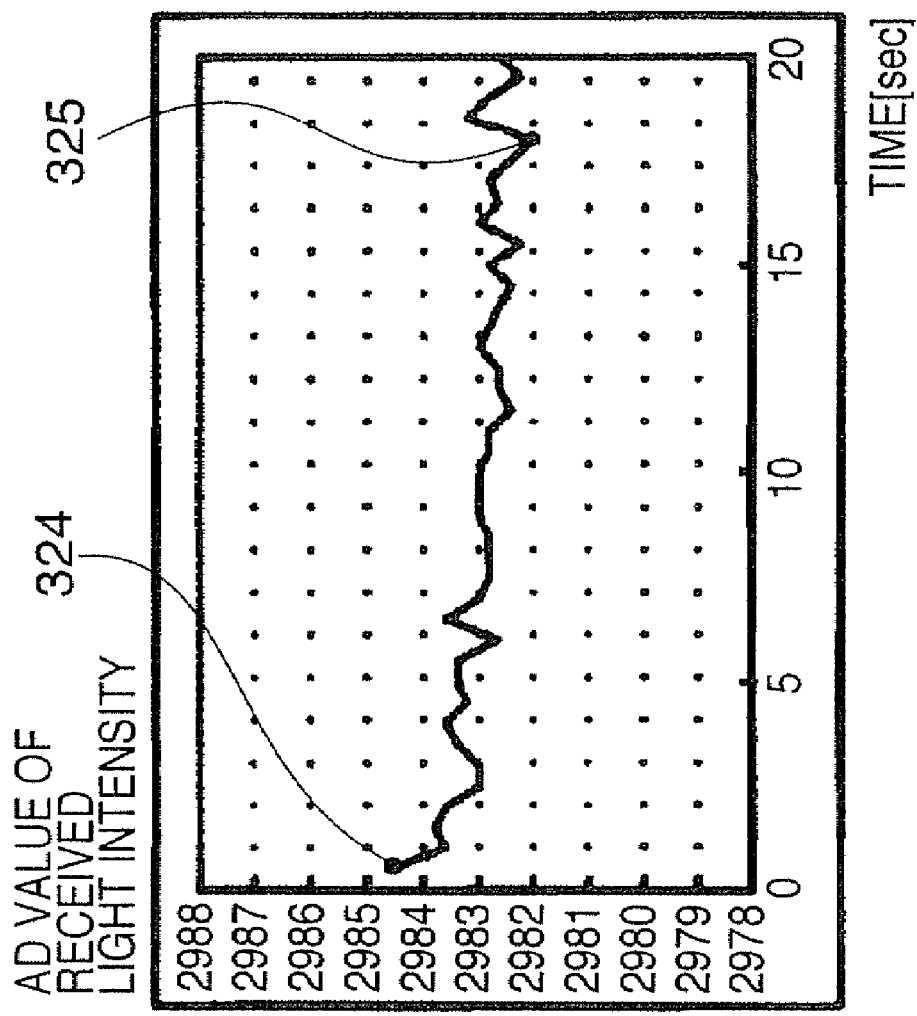
Figure 3H:
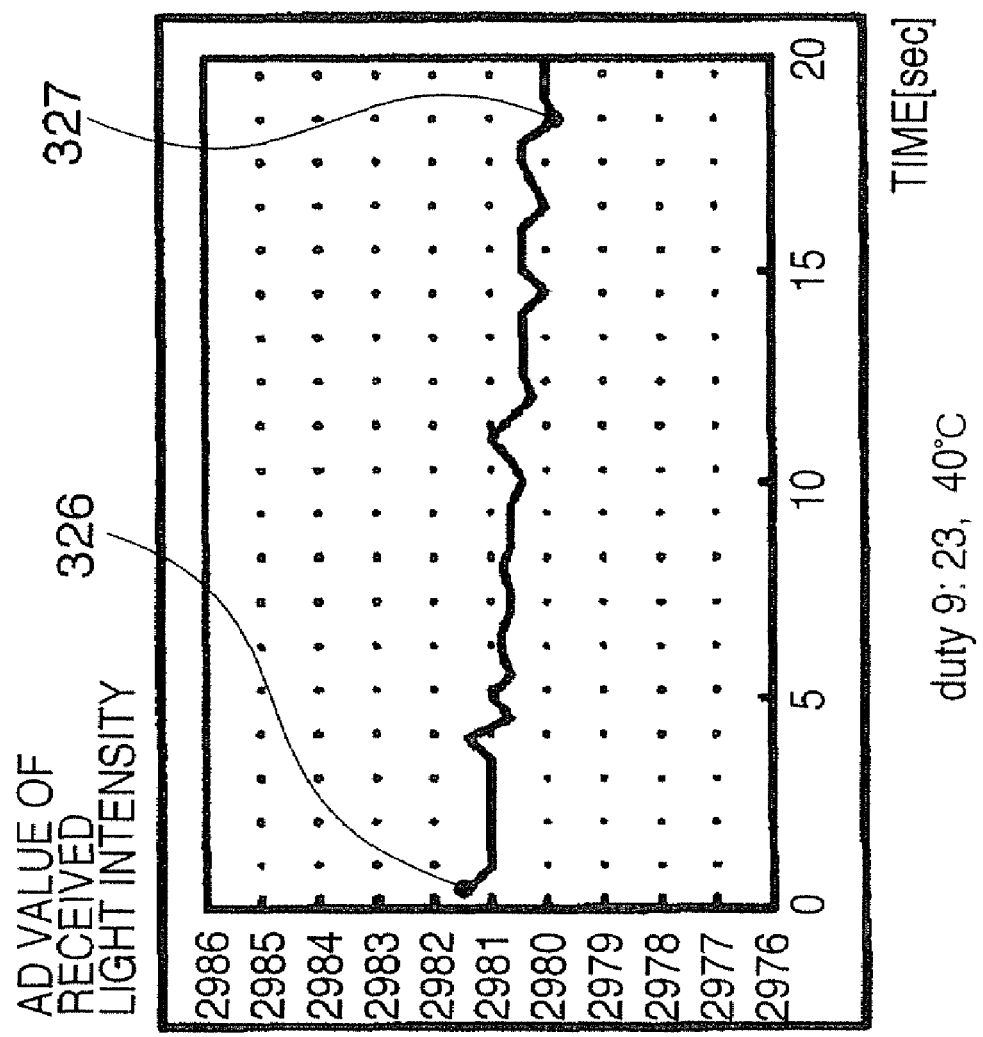

Next, by referring to FIGS. 3A to 3I, it is explained about the emitted light intensity when the pulse width of the light-emitting element is altered according to each of differing ambient temperatures. FIGS. 3A to 3C illustrate a measurement result by the light-receiving element when the pulse width is changed under the ambient temperature of 5° C. Further, FIGS. 3D to 3F illustrate a measurement result by the light-receiving element when the pulse element is changed under the ambient temperature of 25° C. Furthermore, FIGS. 3g to 3I illustrate a measurement result by the light-receiving element when the pulse element is changed under the ambient temperature of 40° C.

These figures show measurement results obtained by driving the light-emitting element 114 in accordance with each duty ratio illustrated in the figures, and measuring the emitted light intensity from the light-emitting element 114 for 20 seconds at 500 msec intervals. In the present invention, 3 patterns of duty ratio, which are ON:OFF=8:24, 9:23, 10:22, are utilized. At this time, the longer the ON period is, the longer the light-emitting period of the light-emitting element 114 is, resulting in promotion of heat generation of the light-emitting element 114 itself. In FIGS. 3A to 3I, the X-axis indicates time (sec), and the Y-axis indicates the output value of the AD conversion unit 110 which expresses brightness level of the reflected light received by the light-receiving element 115.

As shown in FIGS. 3A to 3C, at the ambient temperature of 5° C., when the duty ratio is 8:24 (FIG. 3A), the difference between the maximum value (304) and the minimum value (305) of the output values by the AD conversion unit 110 is small at approximately "1", and the output values represent approximately "2980". Even with other duty ratios, the differences between the maximum values (306, 308) and the minimum values (307, 309) remain small at approximately "1". In other words, regardless of the difference in duty ratios, fluctuation in emitted light intensity can be kept low. Accordingly, during the light intensity stabilization processing, by having the duty ratio of the driving signal 206 as 8:24 and shortening the pulse width, it is possible to suppress fluctuation in light intensity within a short time with considering a viewpoint of electric power consumption.

Further, as illustrated in FIGS. 3D to 3I, the higher the ambient temperature, the larger the fluctuation in measurement data values due to time course. For example, among FIGS. 3D to 3F, the difference between the maximum value 314 and the minimum value 315 at a duty ratio of 8:24 (FIG. 3D) becomes approximately 1.7. Further, when the duty ratio is 9:23 as shown in FIG. 3E, the difference between the maximum value 316 and the minimum value 317 is approximately 1.2. Furthermore, when the duty ratio is 10:22 as shown in FIG. 3F, the difference between the maximum value 318 and the minimum value 319 is approximately 1.2.

Further, among FIGS. 3G to 3I, when the duty ratio is 8:24 (FIG. 3G), the difference between the maximum value 324 and the minimum value 325 is approximately 2.6. Further, when the duty ratio is 9:23 (FIG. 3H), the difference between the maximum value 326 and the minimum value 327 is approximately 1.8. Furthermore, when the duty ratio is 10:22 as shown in FIG. 3I, the difference between the maximum value 328 and the minimum value 329 is approximately 1.2.

As shown here, it can be understood that the difference between the maximum and minimum values of the output values of the AD conversion unit 110 becomes bigger as the ambient temperature gets higher. On the other hand, even when the ambient temperature is high, it can be read from each of these graphs that it is possible to stabilize the output value within a short time from the start of driving by making the duty ratio higher (in other words by making the pulse width larger).

For example, among FIGS. 3G to 3I, the graph of FIG. 3G shows that the output value reaches a maximum value 324 right after the start of measurement and gradually drops, and even after 20 seconds the output value fluctuates considerably. On the other hand, in a graph where the pulse width is set to be large (FIG. 3I), the maximum value 328 is marked right after the start of measurement, and after a lapse of approximately 2 seconds the output value stabilizes in a vicinity of 2977.5.

With this setup, when adjusting the conditions of light emission by altering the pulse width of the driving signal for the light-emitting element 114 during light intensity stabilization processing, the characteristics of light emission by the light-emitting element 114 is not significantly influenced by the conditions of driving when the ambient temperature is low, and therefore a short pulse width can be applied. On the other hand, when the ambient temperature is higher, it is necessary to aggressively drive the light-emitting element 114 to stabilize the light intensity of the emitted light, and therefore a longer pulse width is applied.

As shown, the light intensity stabilization processing according to the present invention can shorten the time required for light intensity stabilization processing by changing the conditions of light emission of the light-emitting element 114 according to the ambient temperature. Note that although the method of changing the pulse width (duty ratio) of the light-emitting element 114 was explained as a condition of light emission, this is only one example and the present invention is not limited to this.

For example, it is also possible to alter the pulse amplitude or pulse period during light emission by the light-emitting element 114 as conditions of light emission of the light-emitting element 114. When changing the pulse amplitude, it is also acceptable to adjust the applied voltage from the usual voltage (corresponding to L1 in FIG. 2B, for example, 2.8V) used for the light emission of the light-emitting element 114 according to the ambient temperature measured. When changing the pulse period, it is also acceptable to change the intervals of light emission from 500 msec to 300 msec. Further, it is also possible to control the execution time of the light intensity stabilization processing without changing the pulse width, pulse amplitude and pulse period. Additionally, it is desirable to classify these conditions of light emission according to the sectionalized ambient temperature and store them in the memory 105. Note that specific numerical values number will be provided in the after-mentioned first and second embodiments.

Figure 4:
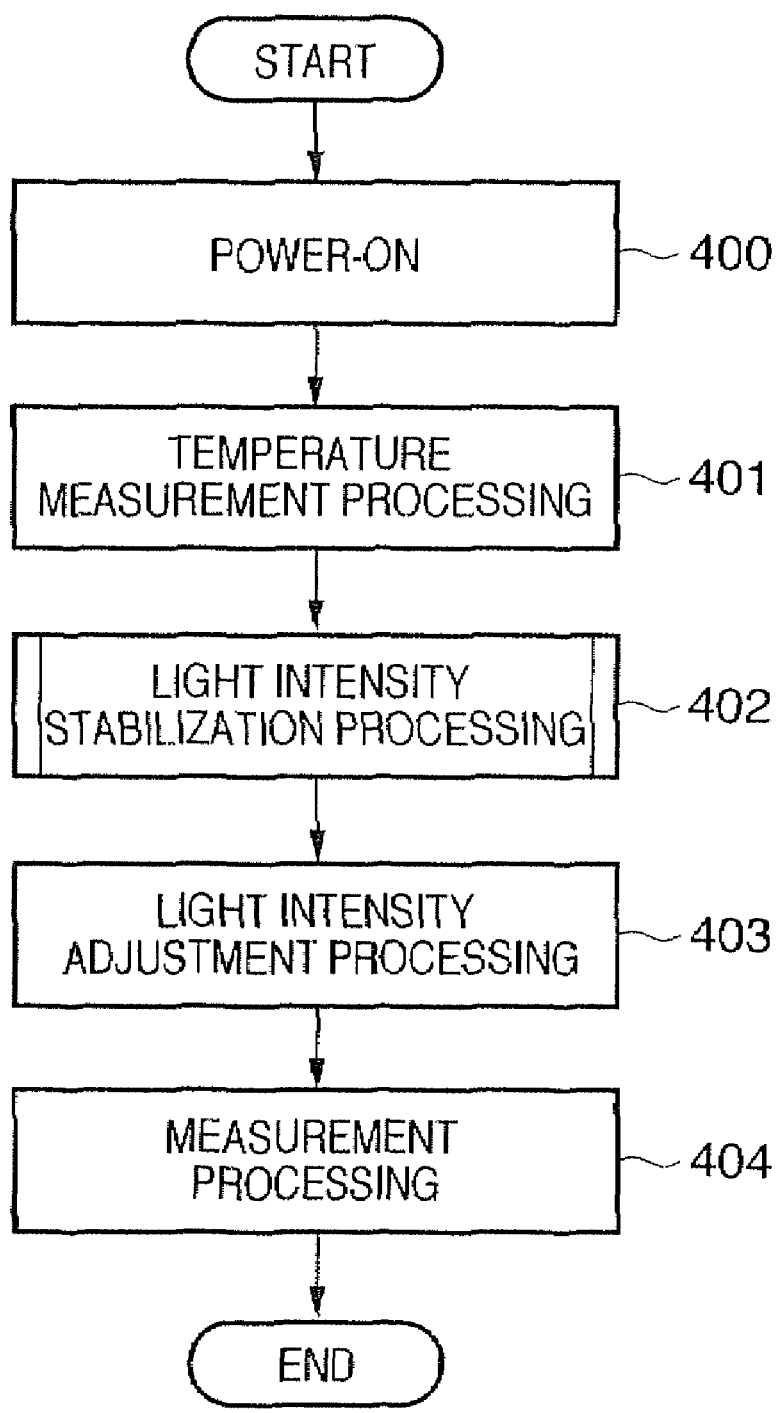
FIG. 4 is a flow chart showing the control of the body fluid constituents measurement device according to the present invention.

Next, with reference to FIG. 4, the flow of processing at the body fluid constituents measurement device 100 according to the present invention will be explained. FIG. 4 shows an exemplary flow of processing from the preprocessing (preparatory) for the measurement processing to the measurement processing itself for the constituent measurement of the body fluid constituents measurement device 100 of the present invention.

When the power is switched on, the CPU 101 commands the temperature measurement unit 111 to measure the ambient temperature at step S401. The temperature measurement unit 111 measures the ambient temperature of the vicinity of the light-emitting element 114 and outputs an analog signal to the AD conversion unit 110. The AD conversion unit 110 converts the inputted analog signals to digital signals and outputs the digital signals to the CPU 101. According to this, the CPU 101 detects the ambient temperature at the time of the body fluid constituent measurement.

When the ambient temperature is measured, the CPU 101 performs light intensity stabilization processing at step S402. At this step, the CPU 101 reads out the conditions of light emission pre-stored in the memory 105 by the determination unit 109, according to the measured ambient temperature, and transmits these conditions of light emission to the driving control unit 107. The driving control unit 107 drives the light-emitting element 114 according to the transmitted conditions of light emission. The details of light intensity stabilization processing will be described hereinafter using FIGS. 5 and 6.

When the light intensity of the light-emitting element 114 is stabilized, the CPU 101 performs the light intensity adjustment processing at stage S403. During the light intensity adjustment processing, adjustment of light intensity during measurements is performed according to the measured ambient temperature. In other words, the CPU 101 adjusts electric power supplied to the light-emitting element 114 during emission of light according to the measured ambient temperature. The value of the adjusted electric power is transmitted to the driving control unit 107. For example, when the usual electric power value of 2.8 V is used and the measured ambient temperature is 40° C., the electric power is adjusted by 3.0 V. Such light intensity adjustment processing is performed in order to suppress fluctuations in measurement results arising from differences in the ambient temperature, and aims to carry out measurements under conditions which are as same as possible by adjusting the electric power for light emission. Note that it is preferable to store the electric power value used at the time of measurement according to the ambient temperature in the memory 105 preliminarily.

When the preprocessing (preparatory) steps of S401 to S403 are completed, the CPU 101 at step S404 transmits the electric power value adjusted at S403 to the driving control unit 107 and initiates measurement processing of the body fluid constituent. When the measurement processing is initiated, the reflected light of light emitted from the light-emitting unit 114 toward the test paper 117 is received by the light receiving unit 115. The CPU 101 then receives a measurement result via the amplifying unit 108 and the AD conversion unit 110. The received result is allowed to be stored in the memory 105. Further, the CPU 101 is allowed to display the measurement result using at least one of the audio output unit 112 and the display unit 113. Furthermore, the CPU 101 is allowed to transmit the measurement result to the output unit 103.

Figure 5:
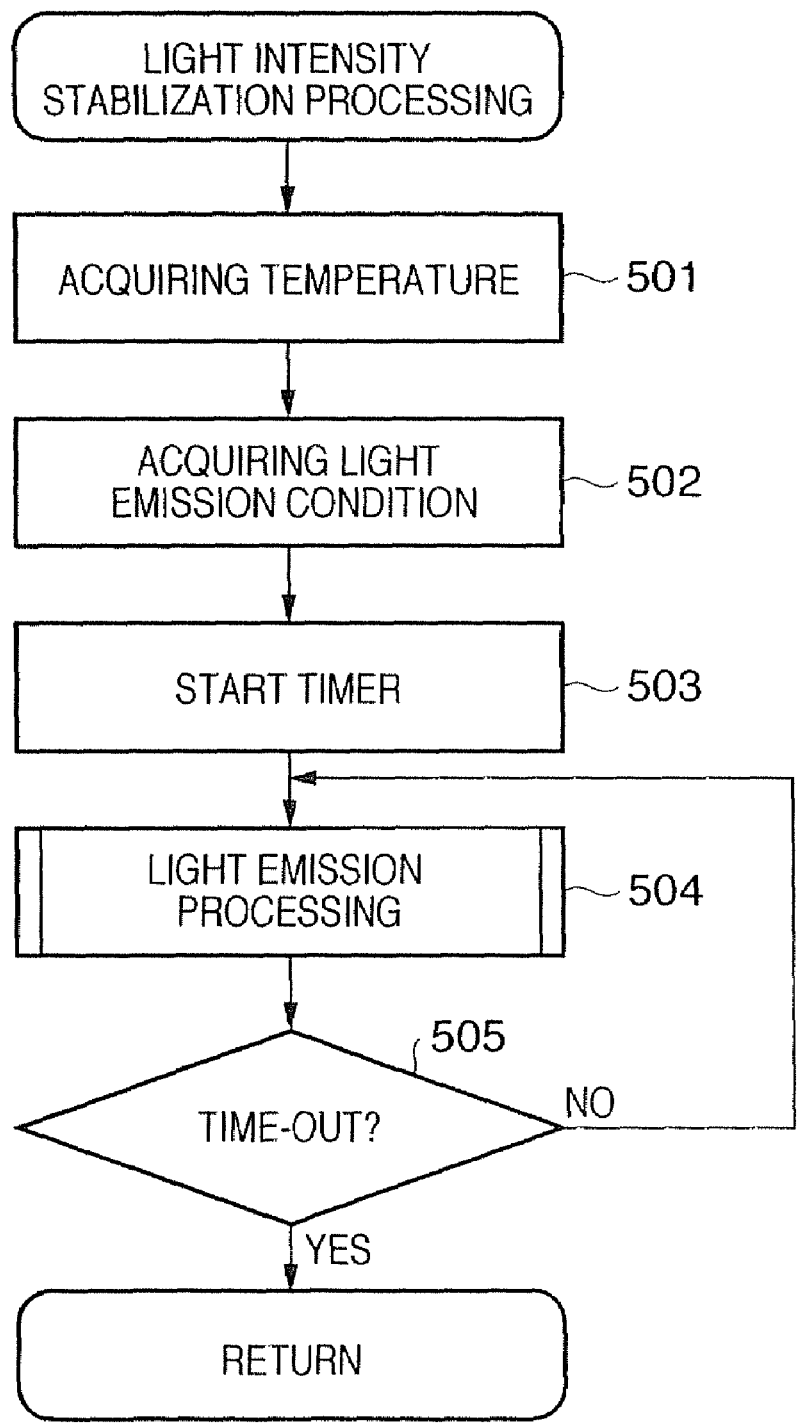
FIG. 5 is a flow chart showing the light intensity stabilization processing according to the present invention.

Next, with reference to FIG. 5, the contents of light intensity stabilization processing performed at step S402 of FIG. 4 will be explained. FIG. 5 is a flow chart showing an example of the light intensity stabilization processing according to the present invention. A case in which the duty ratio is utilized as a condition of light emission during the light intensity stabilization processing will be explained.

At step S501, the CPU 101 acquires the ambient temperature measured by the temperature measurement unit 111. Next, at step S502, CPU 101 acquires the condition of light emission corresponding to the measured ambient temperature from the memory 105. In the memory 105, data such as the optimum duty ratios for every 5° C. is stored, and the CPU 101 reads out the duty ratio which corresponds to the measured ambient temperature. Further, at step S503, the CPU 101 transmits a command to initiate timekeeping to the timer 104. The timekeeping in this context refers to the measurement of time for performing the light intensity stabilization processing, and a predetermined period of time, such as 2 seconds, is measured.

Next, at step S504, the CPU 101 transmits the duty ratio to the driving control unit 107, and commands initiation of light emission processing at the light-emitting element 114. Afterwards, when the light emission processing is performed by the driving control unit 107, the CPU 101 at step S505 determines whether the timer started at S503 has timed out. If timed out, the CPU 101 terminates the light intensity stabilization processing. On the other hand, if not timed out yet, the CPU 101 performs the light emission processing of S504 once again. Note that the CPU 101 repeatedly performs the light emission processing until a timeout has been determined at S505.

Figure 6:
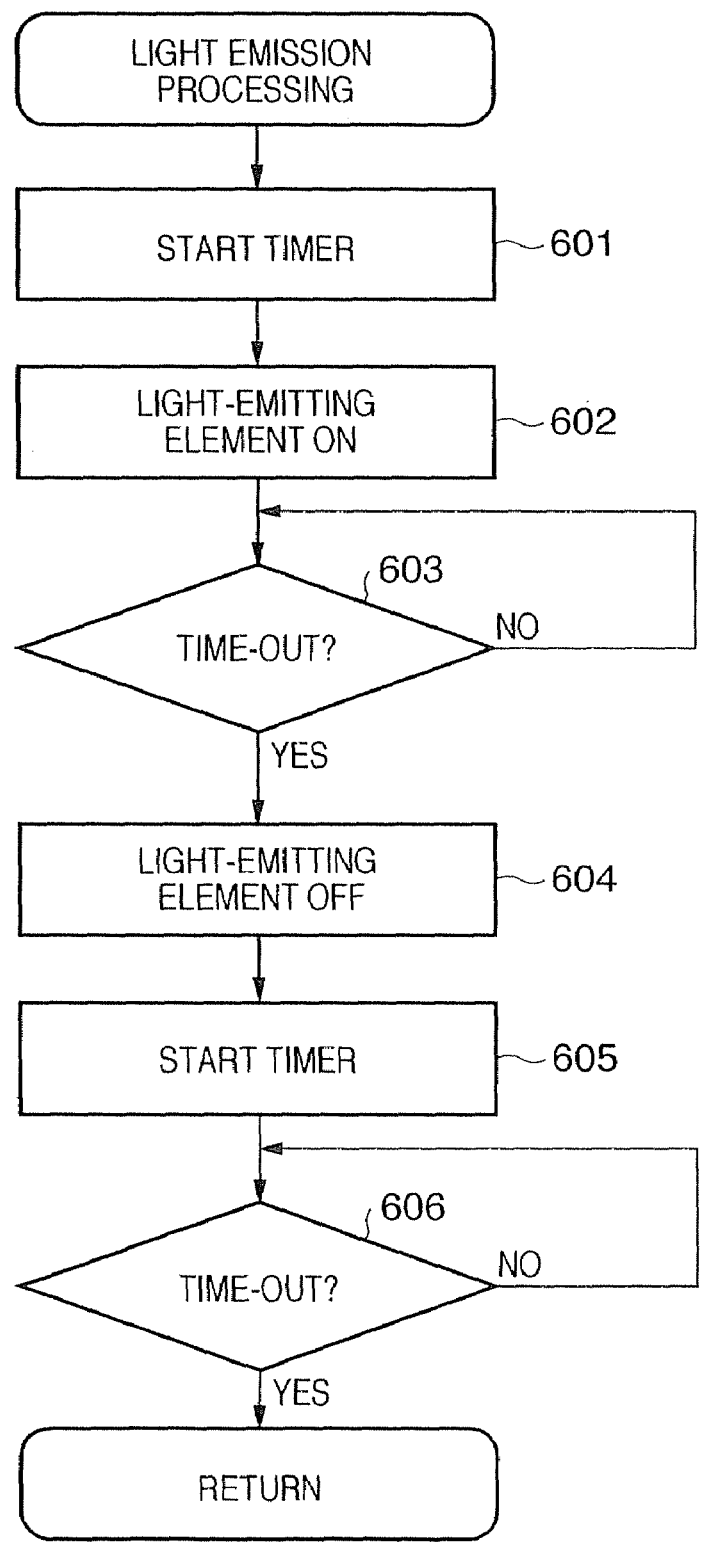
FIG. 6 is a flow chart showing the light emission process of the light-emitting element of the present invention.

Next, referring to FIG. 6, details of the light emission processing at the light-emitting element 114 at step S504 of FIG. 5 is explained. FIG. 6 is a flow chart which illustrates an example of the light emission processing.

During the light emission processing, the driving control unit 107 drives the light-emitting element 114 based on the conditions of light emission received from the CPU 101, such as the ratio of ON and OFF one time. In step S601, the driving control unit 107 commands the timer 104 to initiate timekeeping in order to measure time of the light-emitting element 114 being ON (during which the light-emitting element 114 is put in a state of emitting light). Next, in step S602, the driving control unit 107 controls the light-emitting element 114 to be ON and puts the light emitting element 114 into a light-emitting state.

Subsequently, in step S603, it is determined whether the timer which was initiated for timekeeping at S601 has timed out or not. If timed out, the driving control unit 107 controls the light-emitting element 114 to be OFF and stops light emission at step S604. On the other hand, if not timed out, the driving control unit 107 repeatedly performs the determination of S603 until timeout takes place.

Next, at step S605, the driving control unit 107 commands initiation of timekeeping to the timer 104 to measure time of the light-emitting element 114 being OFF (during which the light-emitting element 114 is put in a state where light emission is arrested). Subsequently, at step S606, the driving control unit 107 determines whether the timer initiated at S605 has timed out or not. If timed out, the driving control unit 107 terminates processing. On the other hand, if not timed out, the driving control unit 107 repeatedly performs the determination of S606 until timeout takes place. Such light emission processing by the driving control unit 107 is repeatedly performed by S504 shown in FIG. 5 while the light intensity stabilization processing is continued.

First Embodiment

Next, referring to FIGS. 7 to 11, a first embodiment will be explained using concrete numerical values. The present embodiment is characterized in that the duty ratio (pulse width), pulse amplitude and pulse period are fixed during the light intensity stabilization processing, and the time (predetermined period of time) of light intensity stabilization processing is altered based on the ambient temperature. Note that from here on, only the parts which are different from those already explained in FIGS. 1 to 6 will be explained.

FIG. 7 shows an exemplary driving pulse of the light-emitting element 114 during measurement of a body fluid constituent according to the first embodiment of the present invention. 710 indicates driving pulses for light intensity stabilization processing, light intensity adjustment processing and measurement. 701 indicates a pulse group including a plurality of pulses outputted during the light intensity stabilization processing. 702 indicates a pulse group outputted during the light intensity adjustment processing and measurement. Further, 711 indicates the detail of the pulse group outputted during the light intensity stabilization processing. Note that pulse driving during light intensity stabilization processing exerts little load on the light-emitting element in comparison to continuous driving as will be explained later, leading to extended life of the light emitting element.

As indicated in FIG. 7, the pulse outputted during the light intensity stabilization processing according to the present embodiment, has a fixed duty ratio of 1:1 and also have the fixed pulse period and fixed pulse amplitude. Specifically, the pulse outputted during the light intensity stabilization processing according to the present embodiment has the ON period of 120 µsec and OFF period of 120 µsec. However, the number of pulse generation during the light intensity stabilization processing is adjusted according to the ambient temperature in the present embodiment. In other words, by changing the number of pulses included in the pulse group 701, the time of light intensity stabilization processing (total time of light emission at the light-emitting element 114) is altered.

Below, with reference to FIGS. 8A to 10B, the measurement result of the received light intensity will be explained when the light-emitting element 114 was driven by the driving pulse indicated in FIG. 7. FIGS. 8A to 10B indicate measurement results concerning the first embodiment of the received light intensity by each measured at different ambient temperatures. Note that some of the figures includes measurement results of received light intensity when no light intensity stabilization processing was carried out under the same ambient temperature. In the case of not performing light intensity stabilization processing, measurement is done with the ON and OFF period respectively set at 120 µsec and 660 µsec. Further, each of the graphs indicate time on the horizontal axis and received light intensity (AD value) by the light receiving element on the vertical axis.

Figure 8A:
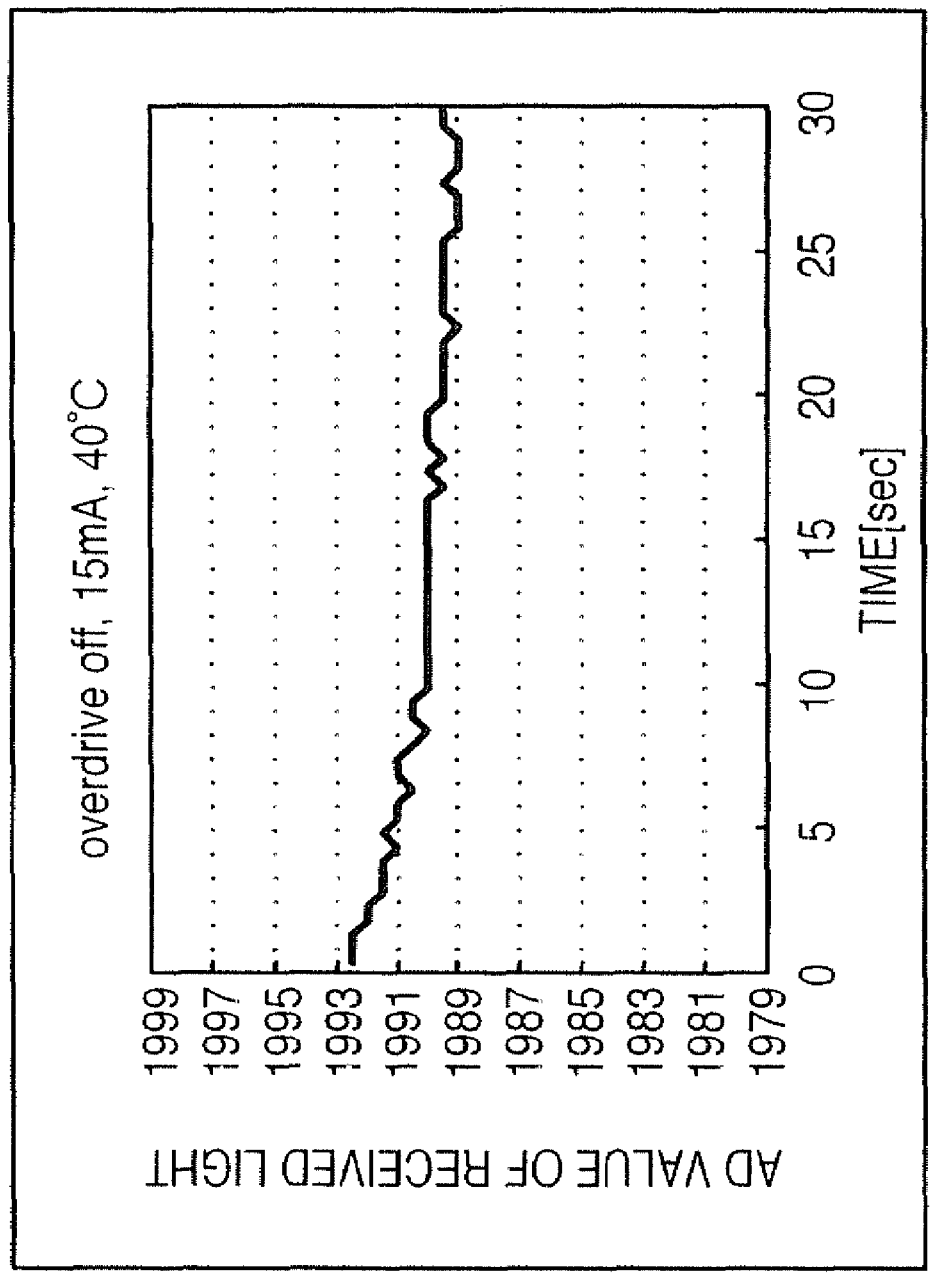
FIGS. 8A and 8B show the measurement results of the received light intensity according to the first embodiment.
Figure 8B:
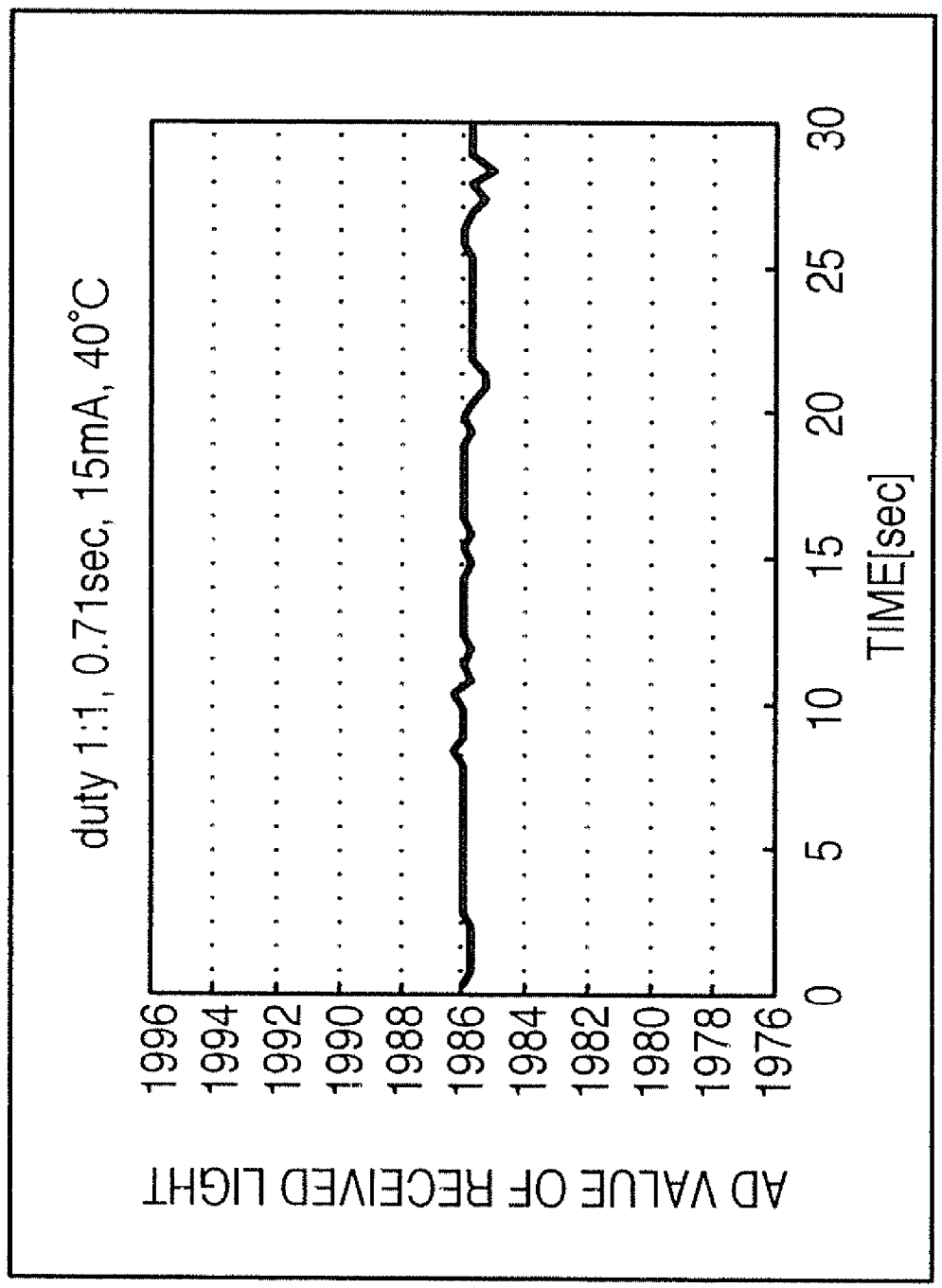

FIG. 8A shows the measurement result of the received light intensity at an ambient temperature of 40° C. when no light intensity stabilization processing was performed and the light-emitting element 114 was driven with 15 mA. FIG. 8B shows the measurement result of the received light intensity at an ambient temperature of 40° C. when light intensity stabilization processing was performed with duty ratio of 1:1 and driving time of 0.71 sec, and the light-emitting element 114 was driven with 15 mA. As shown in FIGS. 8A and 8B, it is obvious that the received light intensity is stabilized when light intensity stabilization processing was performed (FIG. 8B) in contrast to when no light intensity stabilization processing was performed (FIG. 8A). Specifically, when no light intensity stabilization processing was performed, the maximum received light intensity AD value is 1993 and the minimum received light intensity AD value is 1989, the difference between the two values being approximately 4. Further, when no light intensity stabilization process was performed, the time required for stabilization of received light intensity is approximately 25 to 30 seconds. On the other hand, when light intensity stabilization processing was performed, the received light intensity AD value fluctuates near 1986, where the range of fluctuation is small, and the AD value stabilizes after 0.71 sec. In other words, the time needed for stabilization is greatly reduced. In the present embodiment, as shown in FIG. 8B for example, when the fluctuation in the received light intensity AD value converges within 1, the light intensity is determined to have stabilized. This is only an example and does not limit the invention in any way. In other words, the optimal value for the definition of stabilization is preferably defined according to the accuracy of the device element being employed.

Figure 9A:
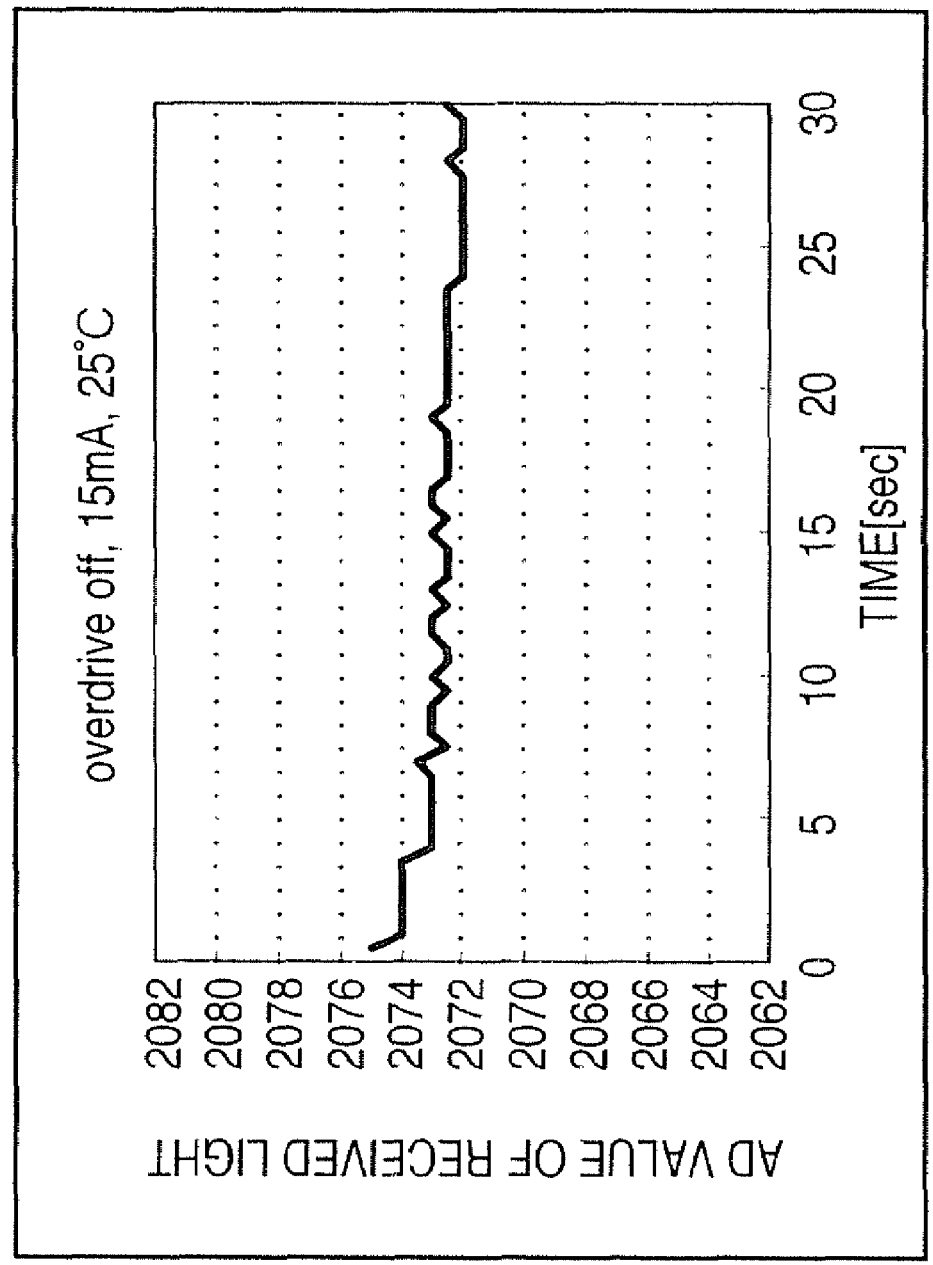
FIGS. 9A and 9B show the measurement results of the received light intensity according to the first embodiment.
Figure 9B:
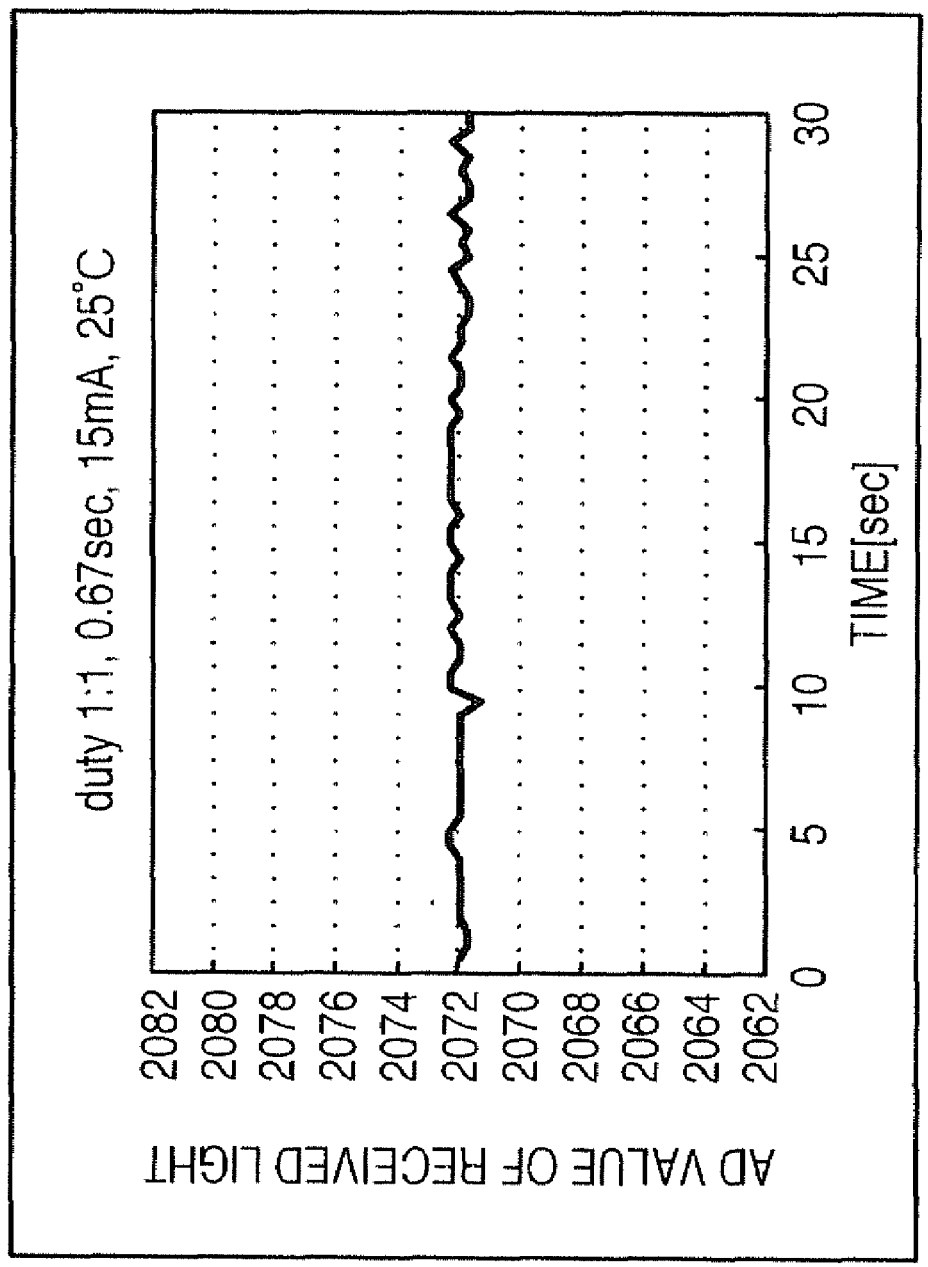

FIG. 9A shows the measurement result of the received light intensity at an ambient temperature of 25° C. when no light intensity stabilization processing was performed and the light-emitting element 114 was driven with 15 mA. FIG. 9B shows the measurement result of the received light intensity at an ambient temperature of 25° C. when light intensity stabilization processing was performed with duty rate of 1:1 and driving time of 0.67 sec, and the light-emitting element 114 was driven with 15 mA. Also in this case, it can be understood that the received light intensity is stabilized when light intensity stabilization processing was performed in contrast to when no light intensity stabilization processing was performed.

Figure 10A:
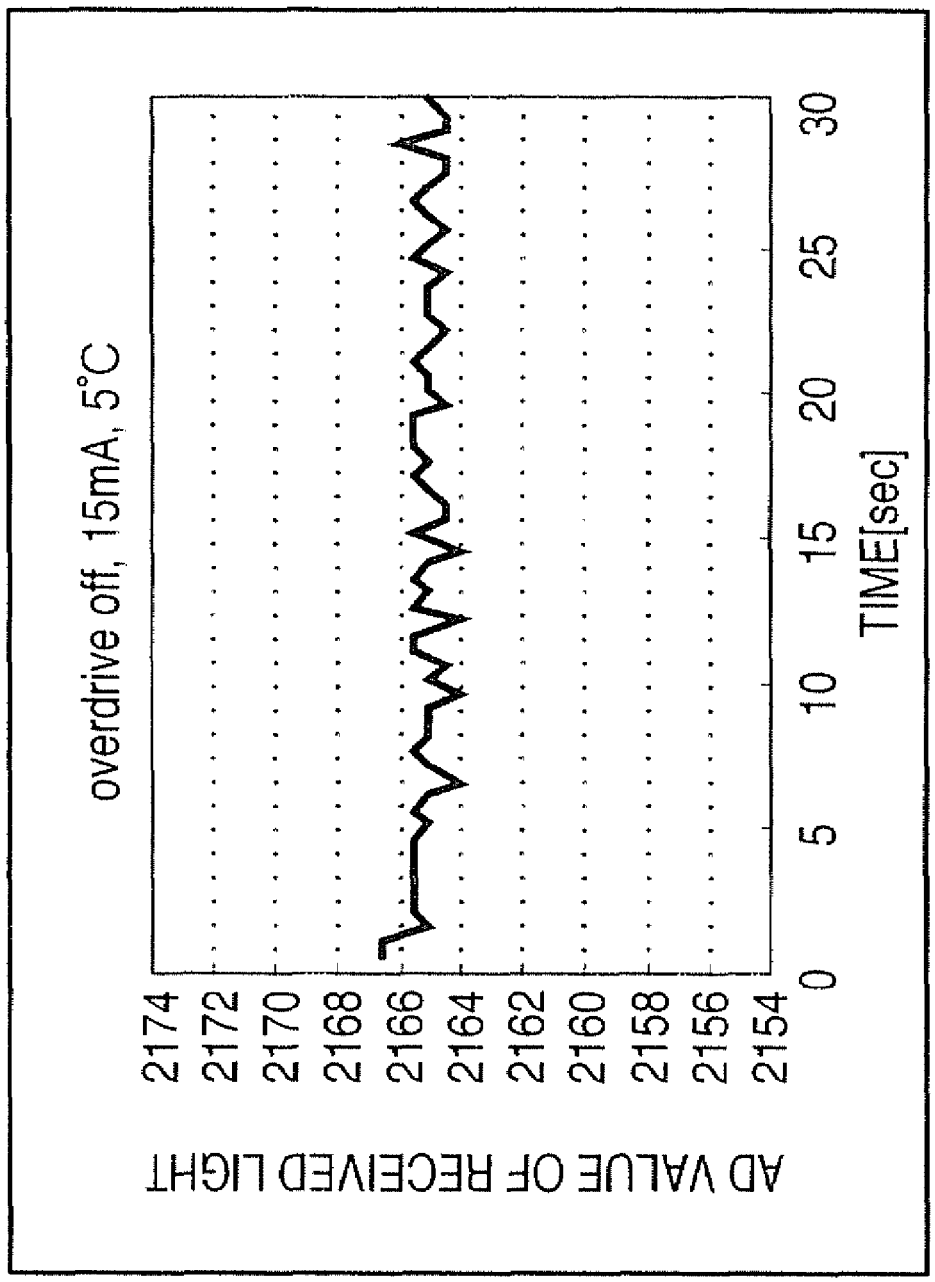
FIGS. 10A and 10B show the measurement results of the received light intensity according to the first embodiment.
Figure 10B:
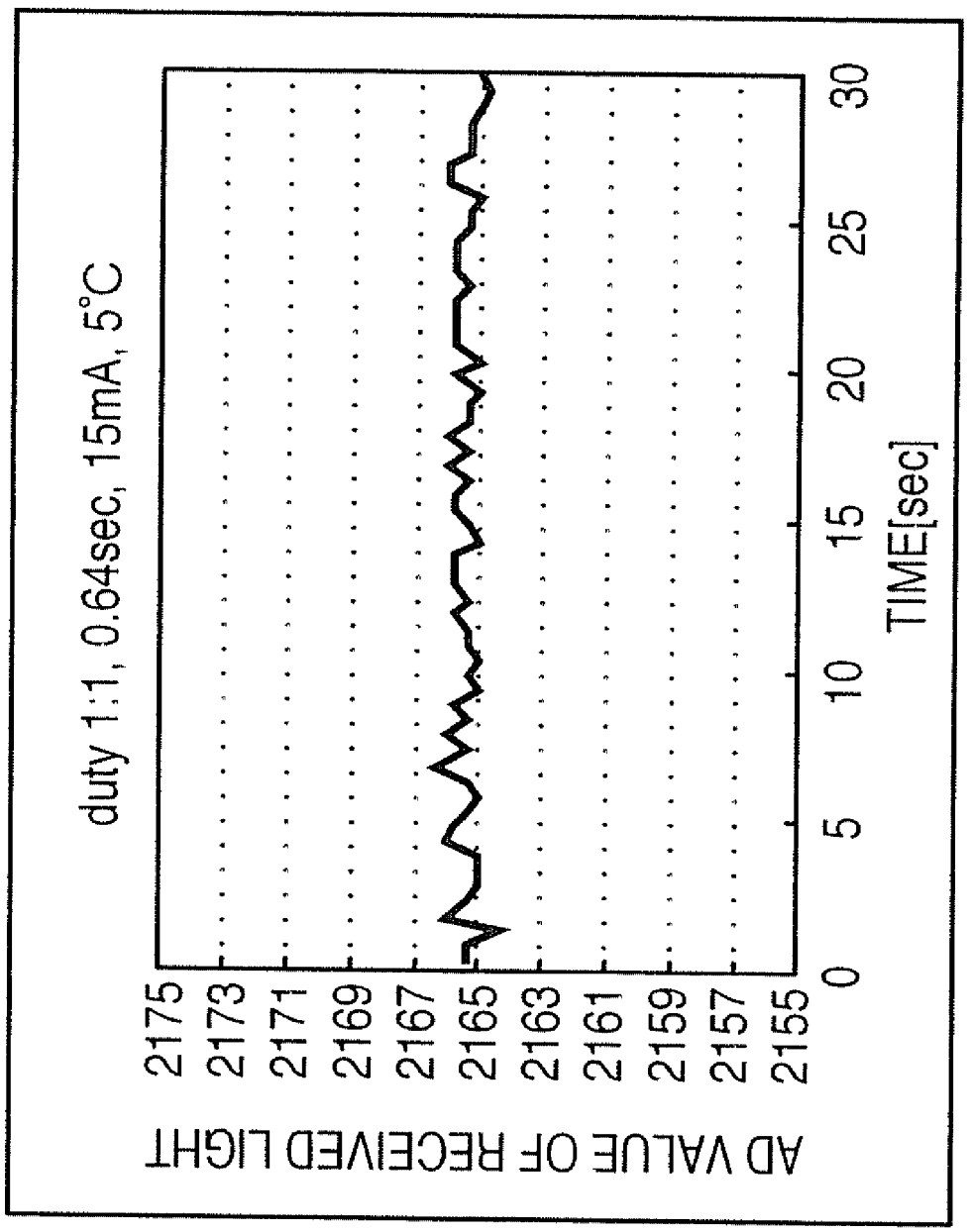

FIG. 10A shows the measurement result of the received light intensity at an ambient temperature of 5° C. when no light intensity stabilization processing was performed and the light-emitting element 114 was driven with 15 mA. FIG. 10B shows the measurement result of the received light intensity at an ambient temperature of 5° C. when light intensity stabilization processing was performed with duty rate of 1:1 and driving time of 0.67 sec, and the light-emitting element 114 was driven with 15 mA. Also in this case, it can be understood that the received light intensity is stabilized when light intensity stabilization processing was performed in contrast to when no light intensity stabilization processing was performed.

Further, as can be understood from FIGS. 8A, 9A and 10A, the lower the ambient temperature, the better stabilized the received light intensity AD value. Based on this, the present embodiment uses shorter driving times for light intensity stabilization processing for lower ambient temperatures. With this, when measuring constituents of body fluid, it is possible to perform light intensity stabilization processing which is appropriate for the measured ambient temperature. Note that in the present embodiment, a table, in which the correspondence of ambient temperature and the driving time of the light-emitting element 114 for light intensity stabilization processing is provided, is prestored in the memory 105. In this case, at S502 of FIG. 5, the CPU 101 (determination unit 109) obtains the driving time corresponding to the measured ambient temperature from the memory 105, and then determines conditions of light emission for light intensity stabilization processing.

Next, with reference to FIG. 11, a table 1100 having the correspondence relation between the ambient temperature and the driving time of the light-emitting element 114 during the light intensity stabilization processing will be explained.

FIG. 11 shows the table 1100 in which the conditions for light emission for the light intensity stabilization processing according to the first embodiment is registered.

The table 1100 which relates ambient temperatures 1101 to their corresponding driving times 1102 of the LED (light-emitting element 114) is stored in the memory 105. The ambient temperatures 1101 are divided and defined in several segments, such as below 5.0° C., 5.1° C. to 10.0° C., . . . 30.1° C. to 35.0° C., and above 35.1° C. Further, the LED driving time 1102 is set for each individual segment of temperature. The CPU 101 obtains the LED driving time 1102 corresponding to the measured ambient temperature from the table 1100 as the condition of light emission of the light-emitting element 114 during the light intensity stabilization processing. In this particular example, the ambient temperature was divided into 5° C. segments. However, this example does not limit the present invention to use of 5° C. segments only, and it is preferable to alter the segment range according to, for example, the accuracy of the device element and the capacity of the memory 105.

As explained above, the body fluid constituents measurement device 100 of the present embodiment determines driving time of the light-emitting element 114 which emits light during the light intensity stabilization processing, by measuring the ambient temperature in the vicinity of the light-emitting element 114. Due to this, the light intensity stabilization processing of the present embodiment can stabilize the light intensity emitted from the light-emitting element 114 in a short time after being switched on, while at the same time preparing to obtain accurate measurement results of the body fluid constituent. Further, when the ambient temperature in the vicinity of the light-emitting element 114 is low, it may suppress power consumption by reducing driving time of the light-emitting element 114.

Further, according to the present embodiment, the total sum of the light emitting time of the light-emitting element 114 during the light intensity stabilization processing is 0.3 to 0.4 seconds (and preferably 0.32 to 0.36 seconds). This value is considered about the differences that exist in LEDs manufactured by various manufacturers, which are to be employed as the light-emitting element 114. Further, the time (predetermined period of time) of the light intensity stabilization processing is 0.3 to 2.0 seconds (preferably, 0.5 to 1.0 second, and when the duty ratio is 1:1, 0.6 to 0.75 seconds). Further, the number of pulses when the duty ratio is 1:1 and the pulse width is 120 μsec is 2600 to 3000.

Second Embodiment

Next, with reference to FIGS. 12 to 16, a second embodiment will be explained. The present embodiment is characterized in that the time of light intensity stabilization processing, the pulse amplitude and the pulse period are fixed, and the duty ratio (pulse width) is altered according to the ambient temperature. Note that from here on, only the parts that are different from those already explained in FIGS. 1 to 6 will be explained.

FIG. 12 shows an exemplary driving pulse of the light-emitting element 114 during measurement of a body fluid constituent according to the second embodiment of the present invention. 1210 shows driving pulses during light intensity stabilization processing, light intensity adjustment processing and measurement. 1201 indicates a pulse group including a plurality of pulses outputted during the light intensity stabilization processing. 1202 indicates a pulse group outputted during the light intensity adjustment processing and measurement. Further, 1211 indicates the detail of the pulse group outputted during the light intensity stabilization processing.

As shown in FIG. 12, the pulses outputted during the light intensity stabilization processing of the present embodiment have the fixed driving time as well as the fixed pulse period and the fixed pulse amplitude. Specifically, the pulses outputted during the light intensity stabilization processing of the present embodiment are changed about the ON period 1203 and OFF period 1204 according to the ambient temperature. In other words, by changing the duty ratio included in the pulse group 1201, the light emitting time of the light-emitting element 114 is altered. Further, according to the present embodiment, the sum of the ON period 1203 and the OFF period 1204 is kept constant.

Below, with reference to FIGS. 13A to 15B, the measurement result of the received light intensity will be explained when the light-emitting element 114 was driven by the driving pulse indicated in FIG. 12. FIGS. 13A to 15B indicate measurement results concerning the second embodiment of the received light intensity by each measured at different ambient temperatures. Note that some of the figures includes measurement results of received light intensity when no light intensity stabilization processing was carried out under the same ambient temperature. In the case of not performing light intensity stabilization processing, measurement is done with the ON and OFF period respectively set at 120 μsec and 660 μsec. Further, each of the graphs indicates time on the horizontal axis and received light intensity (AD value) by the light receiving element on the vertical axis.

Figure 13A:
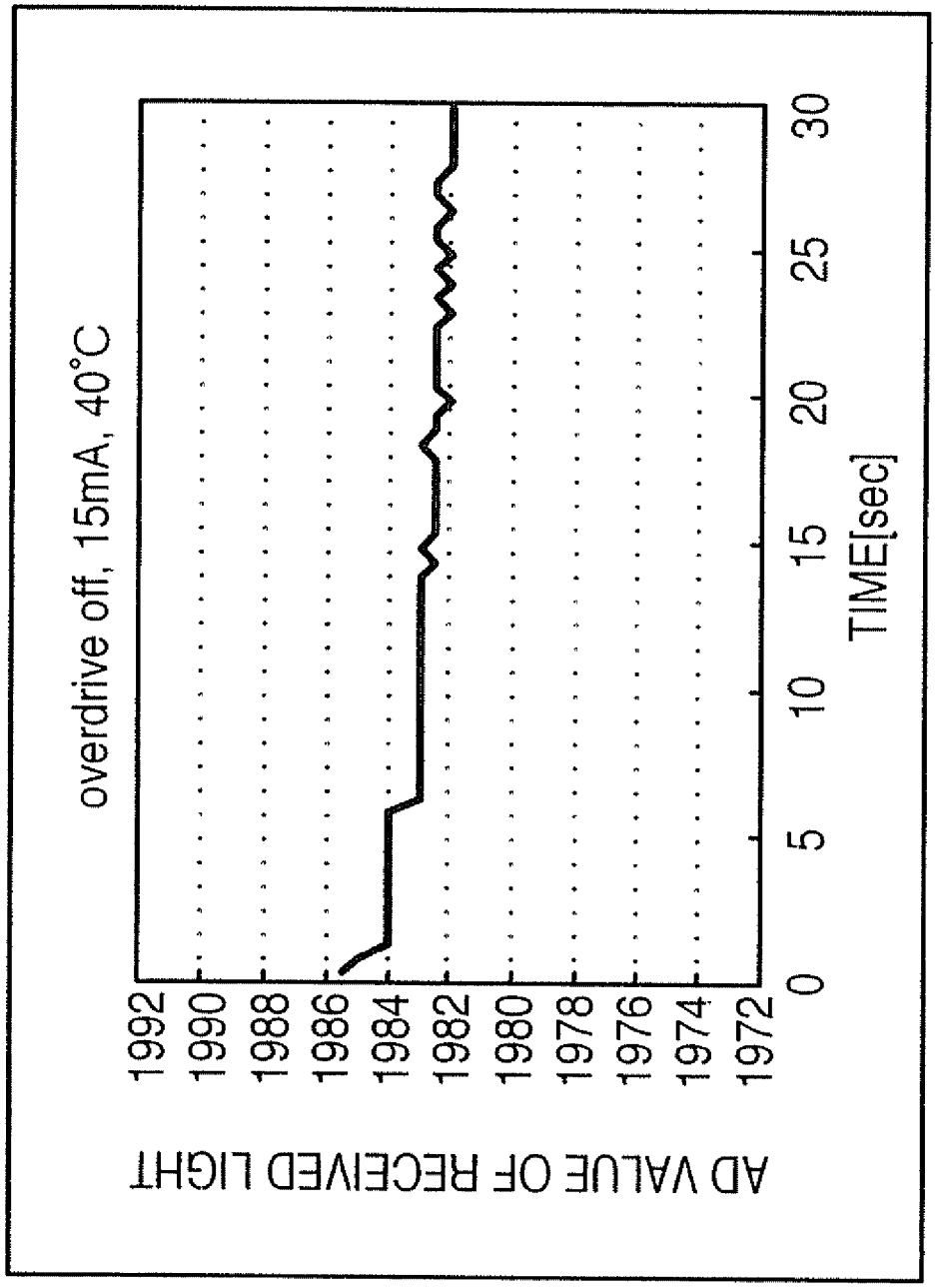
FIGS. 13A and 13B show the measurement results of the received light intensity according to the second embodiment.
Figure 13B:
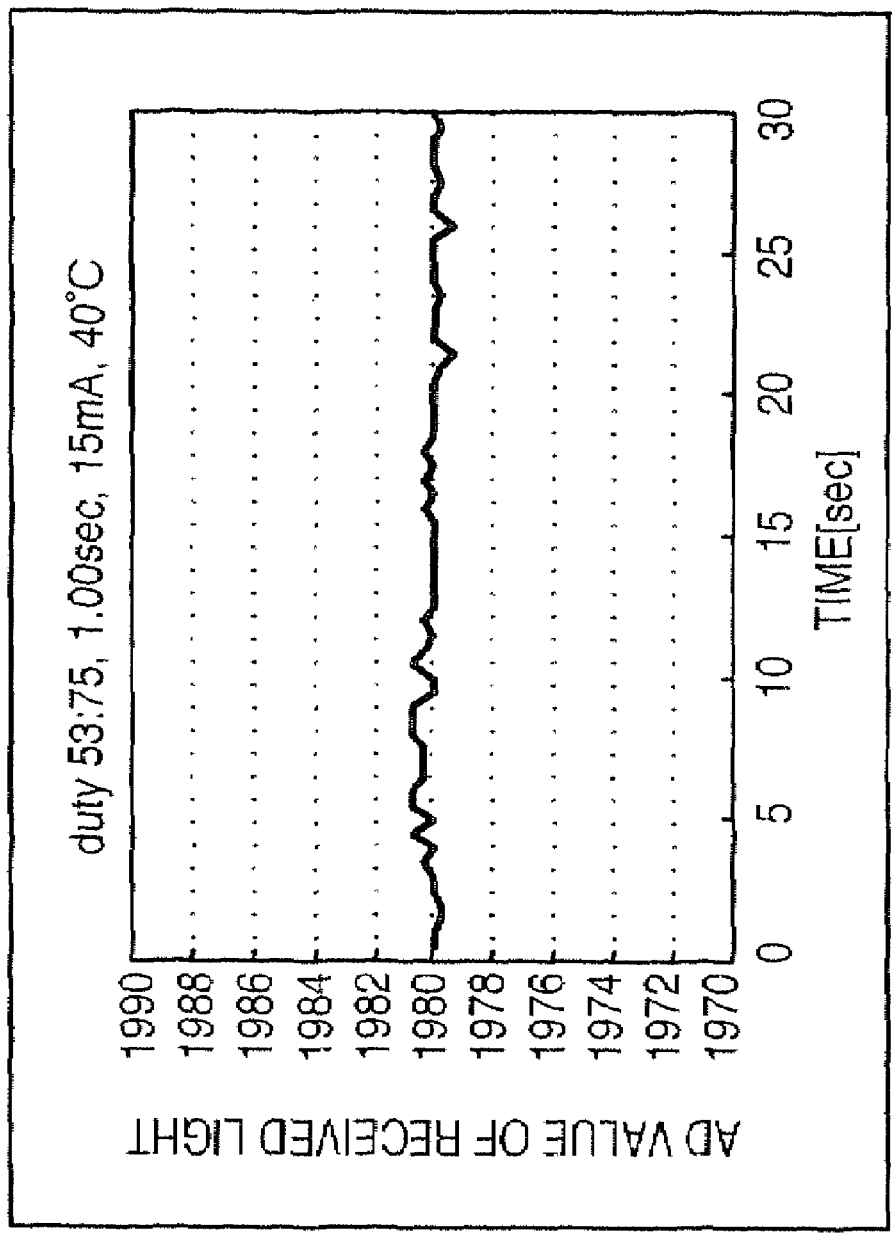

FIG. 13A shows the measurement result of the received light intensity at an ambient temperature of 40° C. when no light intensity stabilization processing was performed and the light-emitting element 114 was driven with 15 mA. FIG. 13B shows the measurement result of the received light intensity at an ambient temperature of 40° C. when light intensity stabilization processing was performed with duty ratio of 53:75 and driving time of 1.00 sec, and the light-emitting element 114 was driven with 15 mA. As shown in FIGS. 13A and 13B, it is obvious that the received light intensity is stabilized when light intensity stabilization processing was performed (FIG. 13B) in contrast to when no light intensity stabilization processing was performed (FIG. 13A). Specifically, when no light intensity stabilization processing was performed, the maximum received light intensity AD value is about 1986 and the minimum received light intensity AD value is about 1982, the difference between the two values being approximately 4. Further, when no light intensity stabilization process was performed, the time required for stabilization of received light intensity is approximately 20 to 30 seconds. On the other hand, when light intensity stabilization processing was performed, the received light intensity AD value fluctuates near 1980, where the range of fluctuation is small, and the AD value stabilizes after 1.00 sec. In other words, the time needed for stabilization is greatly reduced.

Figure 14A:
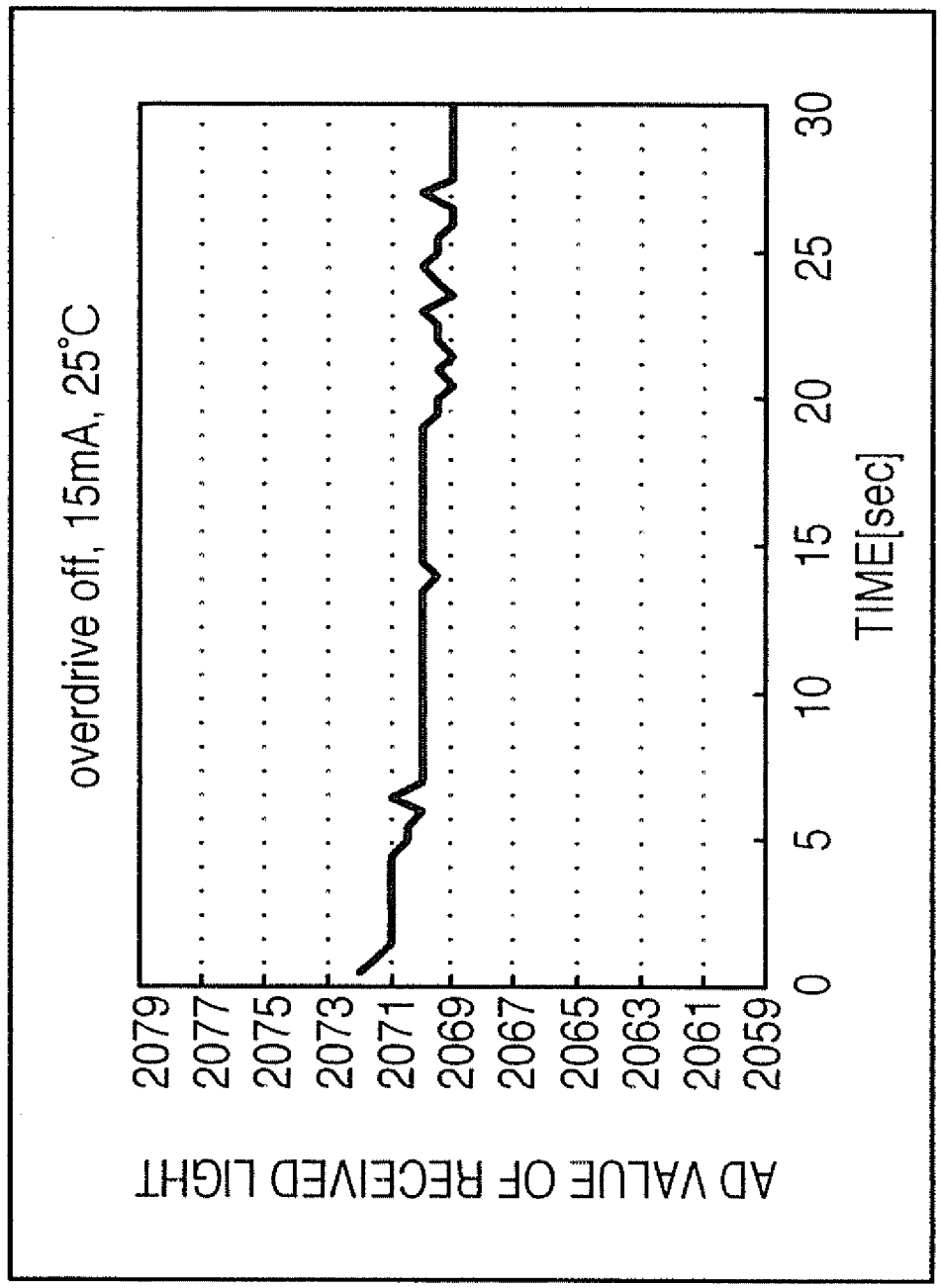
FIGS. 14A and 14B show the measurement results of the received light intensity according to the second embodiment.
Figure 14B:
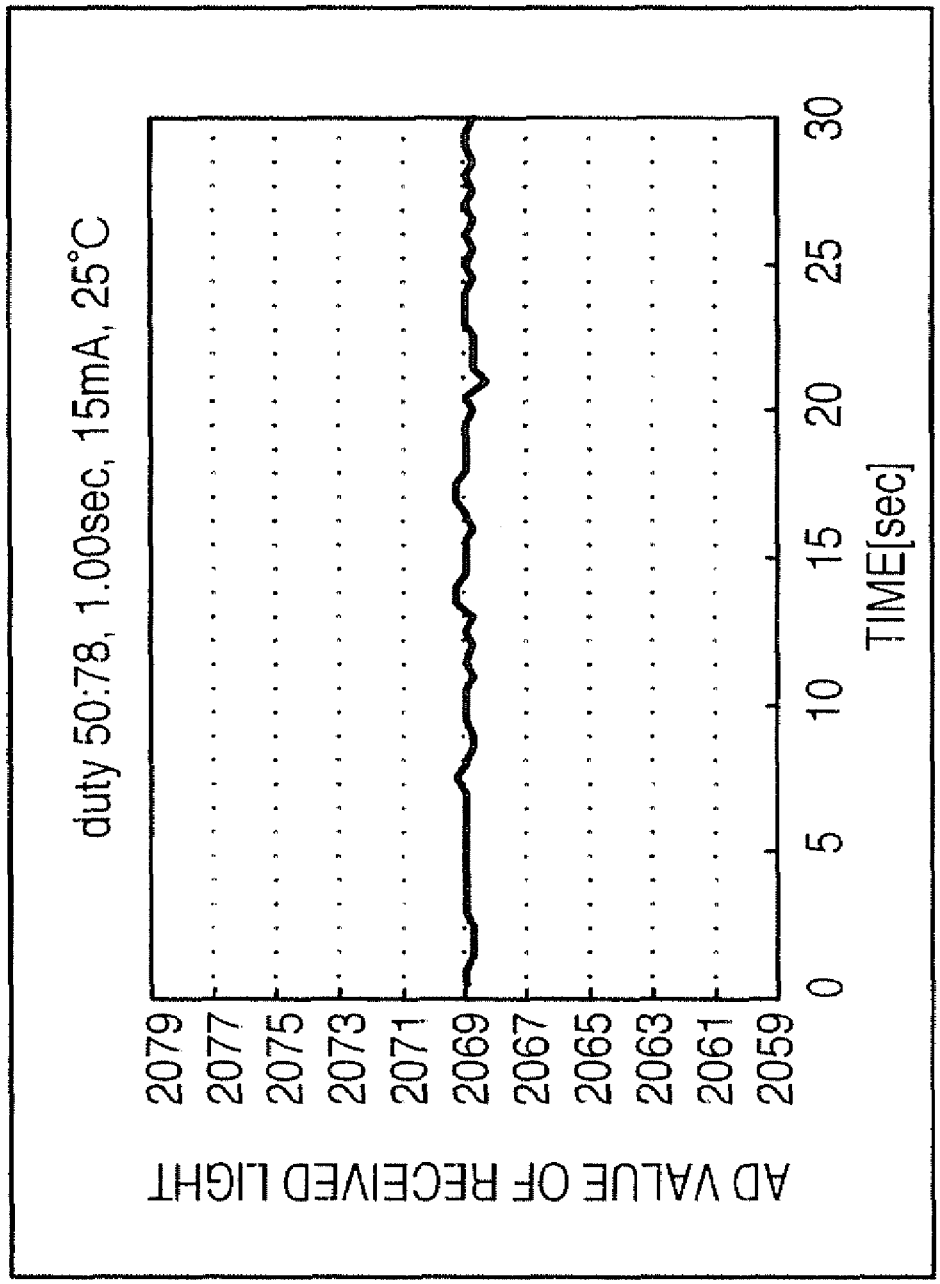

FIG. 14A shows the measurement result of the received light intensity at an ambient temperature of 25° C. when no light intensity stabilization processing was performed and the light-emitting element 114 was driven with 15 mA. FIG. 14B shows the measurement result of the received light intensity at an ambient temperature of 25° C. when light intensity stabilization processing was performed with duty ratio of 50:78 and driving time of 1.00 sec, and the light-emitting element 114 was driven with 15 mA. Also in this case, it can be understood that the received light intensity is stabilized when light intensity stabilization processing was performed in contrast to when no light intensity stabilization processing was performed.

Figure 15B:
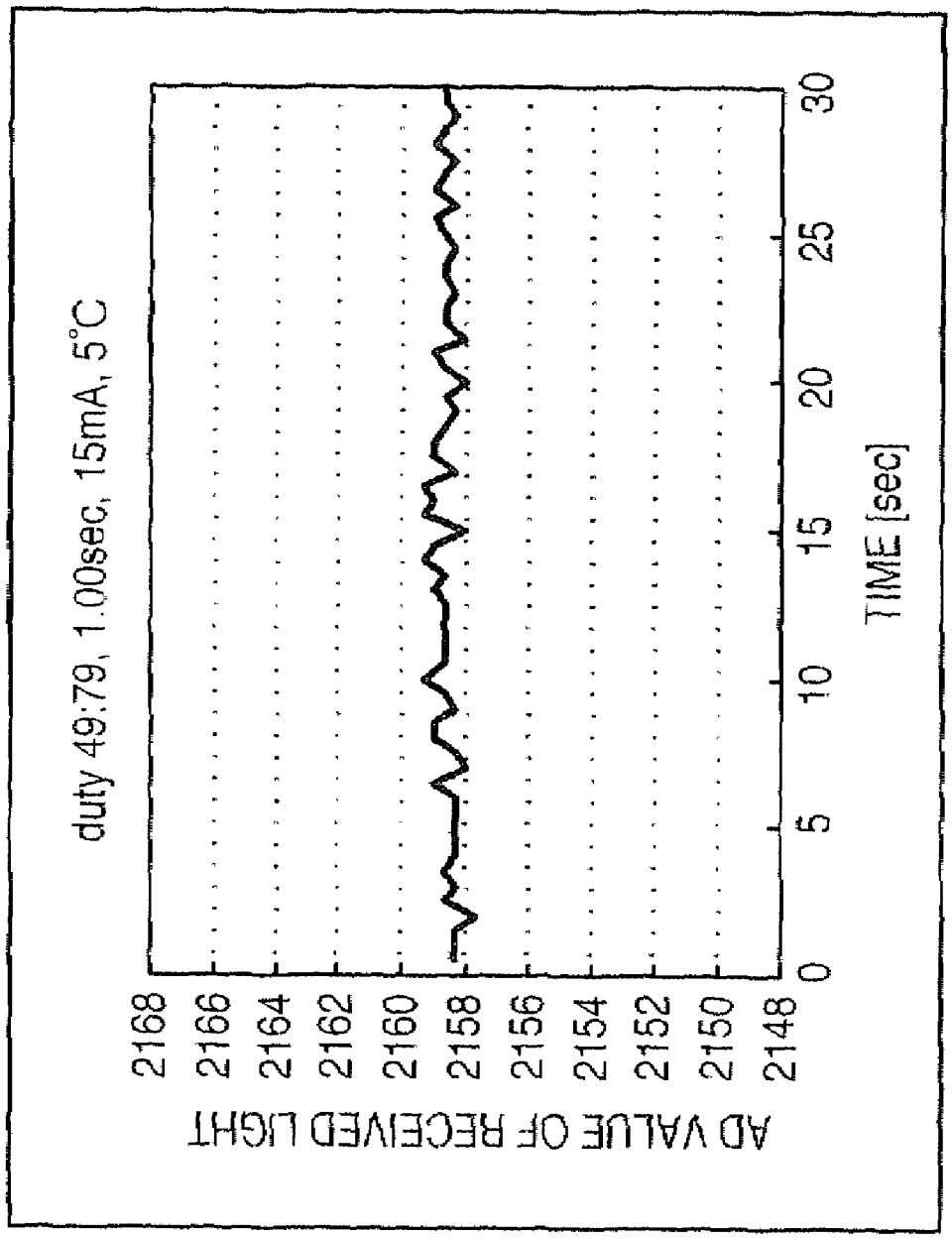

FIG. 15A shows the measurement result of the received light intensity at an ambient temperature of 5° C. when no light intensity stabilization processing was performed and the light-emitting element 114 was driven with 15 mA. FIG. 15B shows the measurement result of the received light intensity at an ambient temperature of 5° C. when light intensity stabilization processing was performed with duty ratio of 49:79 and driving time of 1.00 sec, and the light-emitting element 114 was driven with 15 mA. Also in this case, it can be understood that the received light intensity is stabilized when light intensity stabilization processing was performed in contrast to when no light intensity stabilization processing was performed.

Further, as can be understood from FIGS. 13A, 14A and 15A, the lower the ambient temperature is, the better the received light intensity AD value stabilizes. Based on this, the present embodiment is set to use shorter ON periods of the pulses during light intensity stabilization processing according to lower ambient temperatures. With this, it is possible to perform light intensity stabilization processing which is appropriate for the measured ambient temperature. Note that in the present embodiment, a table, in which the correspondence of ambient temperature and the duty ratio of the driving pulse which drives the light-emitting element 114 during the light intensity stabilization processing is provided, is prestored in the memory 105. In this case, at S502 of FIG. 5, the CPU 101 (determination unit 109) obtains the duty ratio corresponding to the measured ambient temperature from the memory 105, and then determines conditions of light emission for light intensity stabilization processing.

Next, with reference to FIG. 16, a table 1600 having the correspondence between the ambient temperature and the duty ratio of the driving pulse which drives the light-emitting element 114 during the light intensity stabilization processing will be explained. FIG. 16 shows the table 1600 in which the conditions for light emission for the light intensity stabilization processing according to the second embodiment is registered.

The table 1600 which relates ambient temperatures 1601 to their corresponding duty ratios 1602 of the driving pulse which drives the light-emitting element 114 is stored in the memory 105. The ambient temperatures 1601 are divided and defined in several segments, such as below 5.0° C., 5.1° C. to 10.0° C., ... 30.1° C. to 35.0° C., and above 35.1° C. Further, the duty ratio 1602 is set for each individual segment of temperature. The CPU 101 obtains the duty ratio 1602 corresponding to the measured ambient temperature from the table 1600 as the condition of light emission of the light-emitting element 114 during the light intensity stabilization processing. In this particular example, the ambient temperature was divided into 5° C. segments. However, this example does not limit the present invention to use of 5° C. segments only, and it is preferable to adjust the segment range according to, for example, the accuracy of the device element and the capacity of the memory 105.

As explained above, the body fluid constituents measurement device 100 of the present embodiment alters duty ratio of the driving pulse which drives the light-emitting element 114 during the light intensity stabilization processing in accordance with the ambient temperature. Due to this, the light intensity stabilization processing of the present embodiment can stabilize the light intensity emitted from the light-emitting element 114 in a short time after being switched on, while at the same time preparing to obtain accurate measurement results of the body fluid constituent. Further, when the ambient temperature in the vicinity of the light-emitting element 114 is low, it may suppress power consumption by reducing driving time of the light-emitting element 114.

Further, according to the present embodiment, the total sum of the light emitting time of the light-emitting element 114 is 0.3 to 0.5 seconds (and preferably 0.38 to 0.43 seconds) when the light intensity stabilization processing is performed for 1.00 sec. This value is considered about the differences that exist in LEDs manufactured by various manufacturers which are to be employed as the light-emitting element 114. Further, the duty ratio of the pulse for driving the light-emitting element 114 during the light intensity stabilization processing is ON:OFF=5:1 to ON:OFF=1:3 (preferably ON:OFF=2.5:1 to ON:OFF=1:2, when the time of light intensity stabilization processing is 1 sec, ON:OFF=1:1.3 to ON:OFF=1:1.8).

Third Embodiment

Next, with reference to FIGS. 17 to 21, a third embodiment will be explained. The present embodiment is characterized in that the light-emitting element 114 is continuously driven with a fixed pulse amplitude during the light intensity stabilization processing, and the ON period of the pulse driven continuously is altered according to the ambient temperature. Note that from here on, only the parts that are different from those already explained in FIGS. 1 to 6 will be explained.

FIG. 17 shows an exemplary driving pulse of the light-emitting element 114 during measurement of body fluid constituents according to the third embodiment of the present invention. 1710 shows driving pulses during light intensity stabilization processing, light intensity adjustment processing and measurement. 1701 indicates a pulse group including a plurality of pulses outputted during the light intensity stabilization processing. 1702 indicates a pulse group outputted during the light intensity adjustment processing and measurement. Further, 1711 indicates the detail of the pulse group outputted during the light intensity stabilization processing.

As shown in FIG. 17, the pulses outputted during the light intensity stabilization processing of the present embodiment continuously drives the light-emitting element 114. Specifically, the pulse outputted during the light intensity stabilization processing of the present embodiment is altered about the continuous driving time of ON period according to the ambient temperature. In other words, the pulse group 1701 is comprised of a single pulse, and the light emitting time of the light-emitting element 114 is altered by changing the ON period of the single pulse.

Hereinafter, with reference to FIGS. 18A to 20B, the measurement result of the received light intensity will be explained when the light-emitting element 114 was driven by the driving pulse indicated in FIG. 17. FIGS. 18A to 20B show measurement results of the received light intensity by each measured at different ambient temperatures according to the third embodiment. Note that some of the figures also includes measurement results of received light intensity when no light intensity stabilization processing was carried out under the same ambient temperature. In the case of not performing light intensity stabilization processing, measurement is done with the ON and OFF period respectively set at 120 μsec and 660 μsec. Further, each of the graphs indicates time on the horizontal axis and received light intensity (AD value) by the light receiving element 115 on the vertical axis.

Figure 18A:
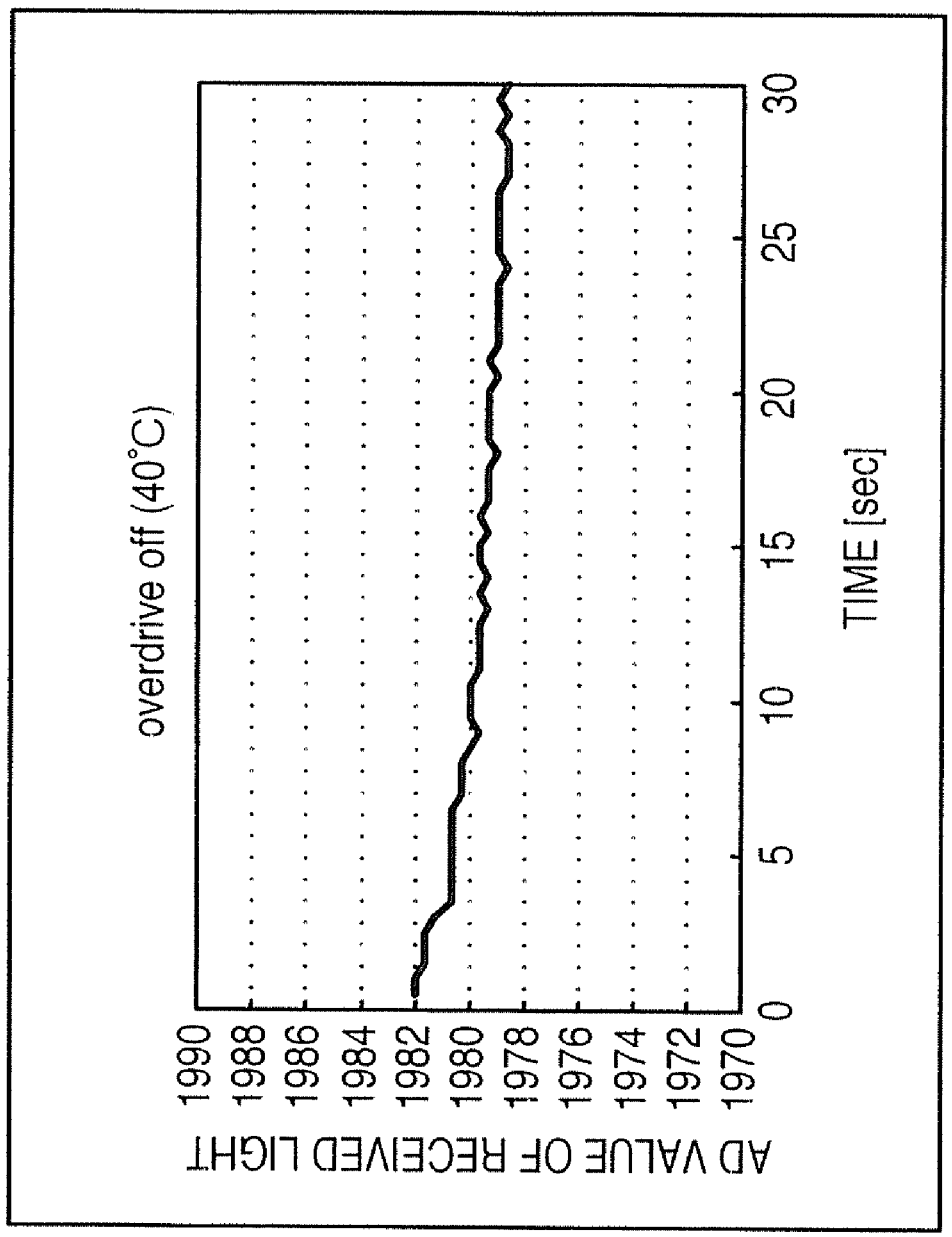
FIGS. 18A and 18B show the measurement results of the received light intensity according to the third embodiment.
Figure 18B:
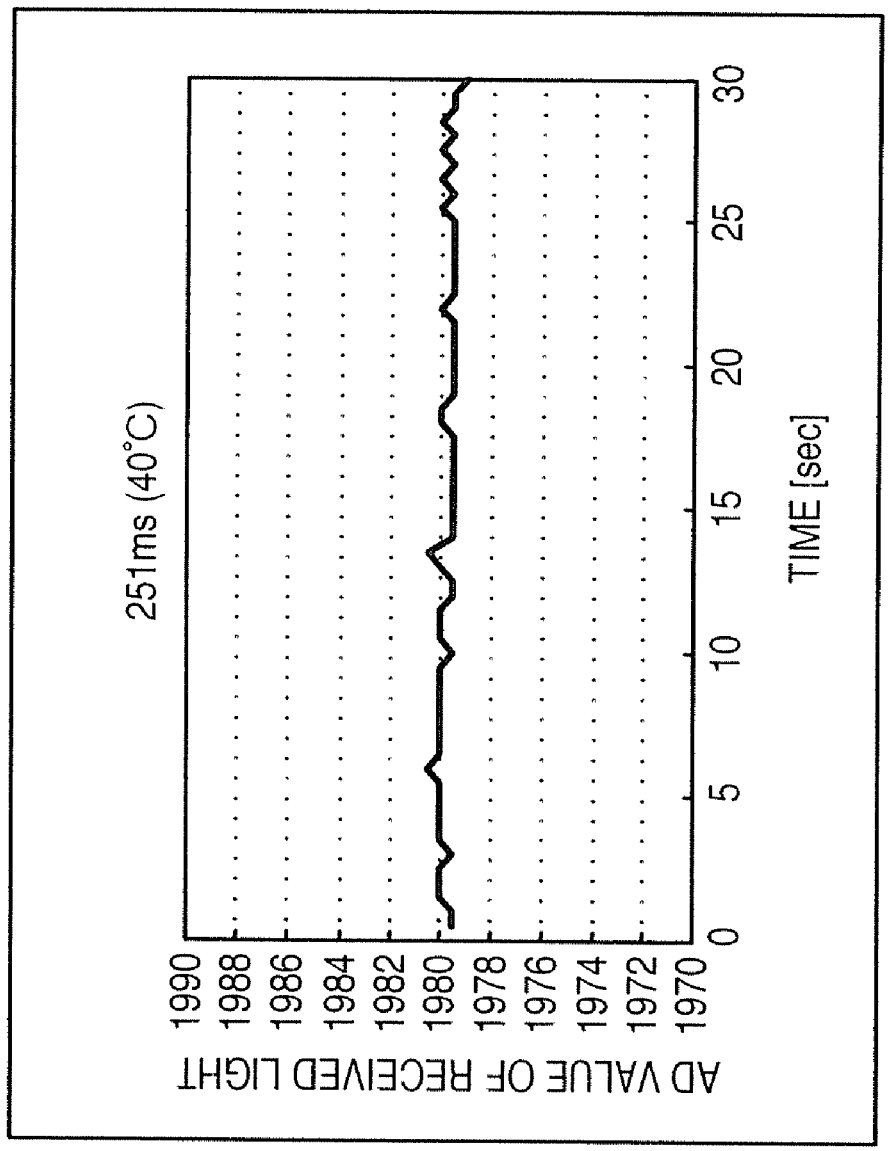

FIG. 18A shows the measurement result of the received light intensity at an ambient temperature of 40° C. when no light intensity stabilization processing was performed and the light-emitting element 114 was driven with 15 mA. FIG. 18B shows the measurement result of the received light intensity at an ambient temperature of 40° C. when light intensity stabilization processing was performed with continuous driving time of 251 msec, and the light-emitting element 114 was driven with 15 mA. As shown in FIGS. 18A and 18B, it is obvious that the received light intensity is stabilized when light intensity stabilization processing was performed (FIG. 18B) in contrast to when no light intensity stabilization processing was performed (FIG. 18A). Specifically, when no light intensity stabilization processing was performed, the maximum received light intensity AD value is about 1982 and the minimum received light intensity AD value is about 1979, the difference between the two values being approximately 3. Further, when no light intensity stabilization process was performed, the time required for stabilization of received light intensity is approximately 20 to 30 seconds. On the other hand, when light intensity stabilization processing was performed, the received light intensity AD value fluctuates near 1980, where the range of fluctuation is small, and stabilizes after 251 msec.

Figure 19A:
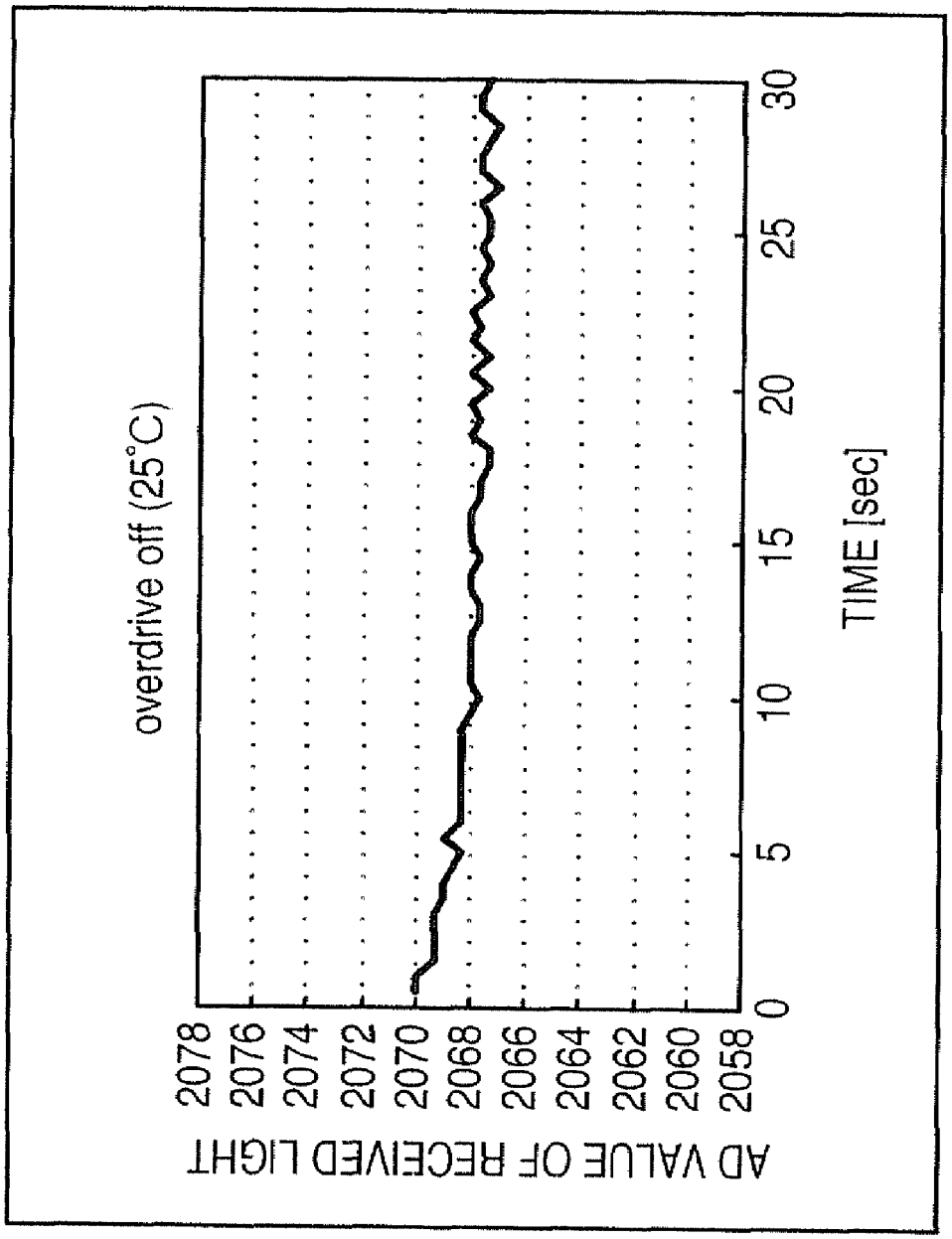
FIGS. 19A and 19B show the measurement results of the received light intensity according to the third embodiment.
Figure 19B:
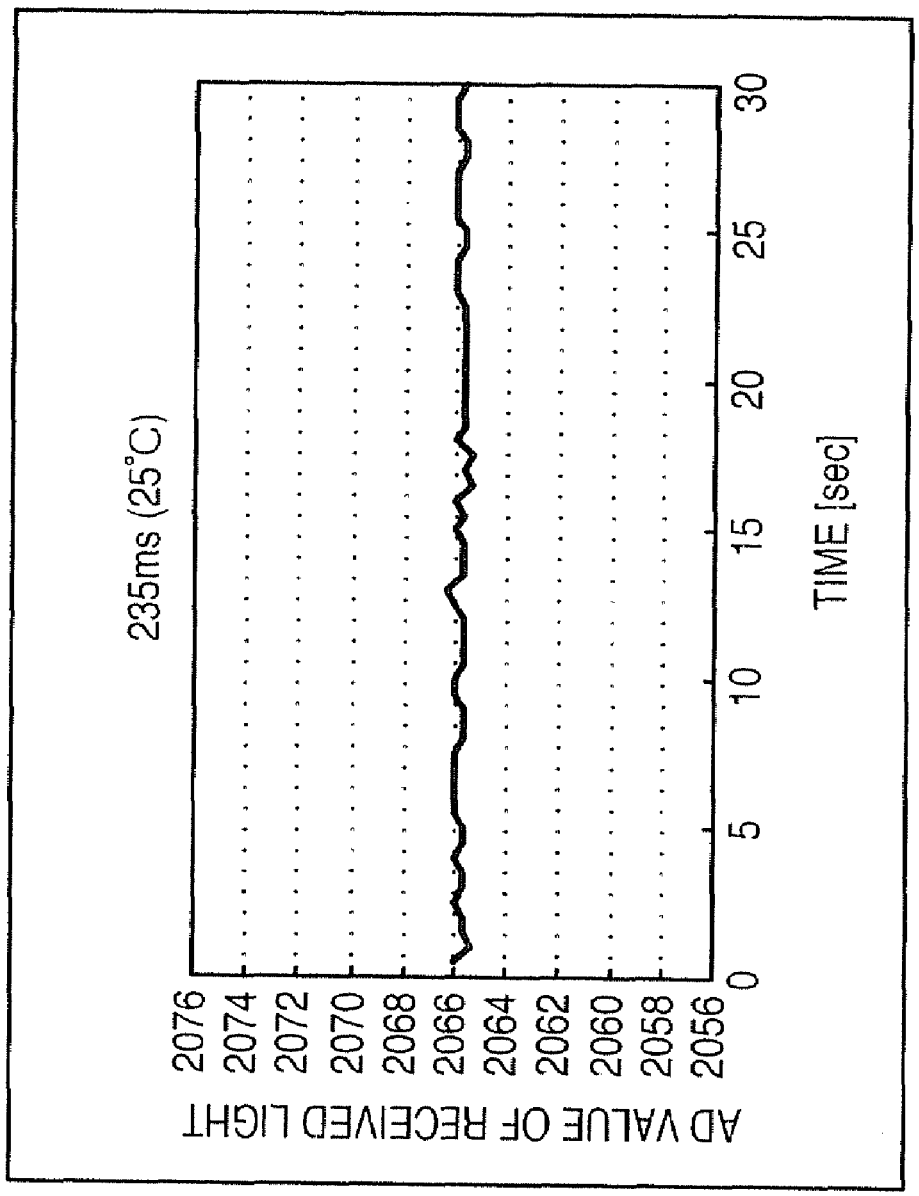

FIG. 19A shows the measurement result of the received light intensity at an ambient temperature of 25° C. when no light intensity stabilization processing was performed and the light-emitting element 114 was driven with 15 mA. FIG. 19B shows the measurement result of the received light intensity at an ambient temperature of 25° C. when light intensity stabilization processing was performed with continuous driving time of 225 msec, and the light-emitting element 114 was driven with 15 mA. Also in this case, it can be understood that the received light intensity is stabilized when light intensity stabilization processing was performed in contrast to when no light intensity stabilization processing was performed.

Figure 20A:
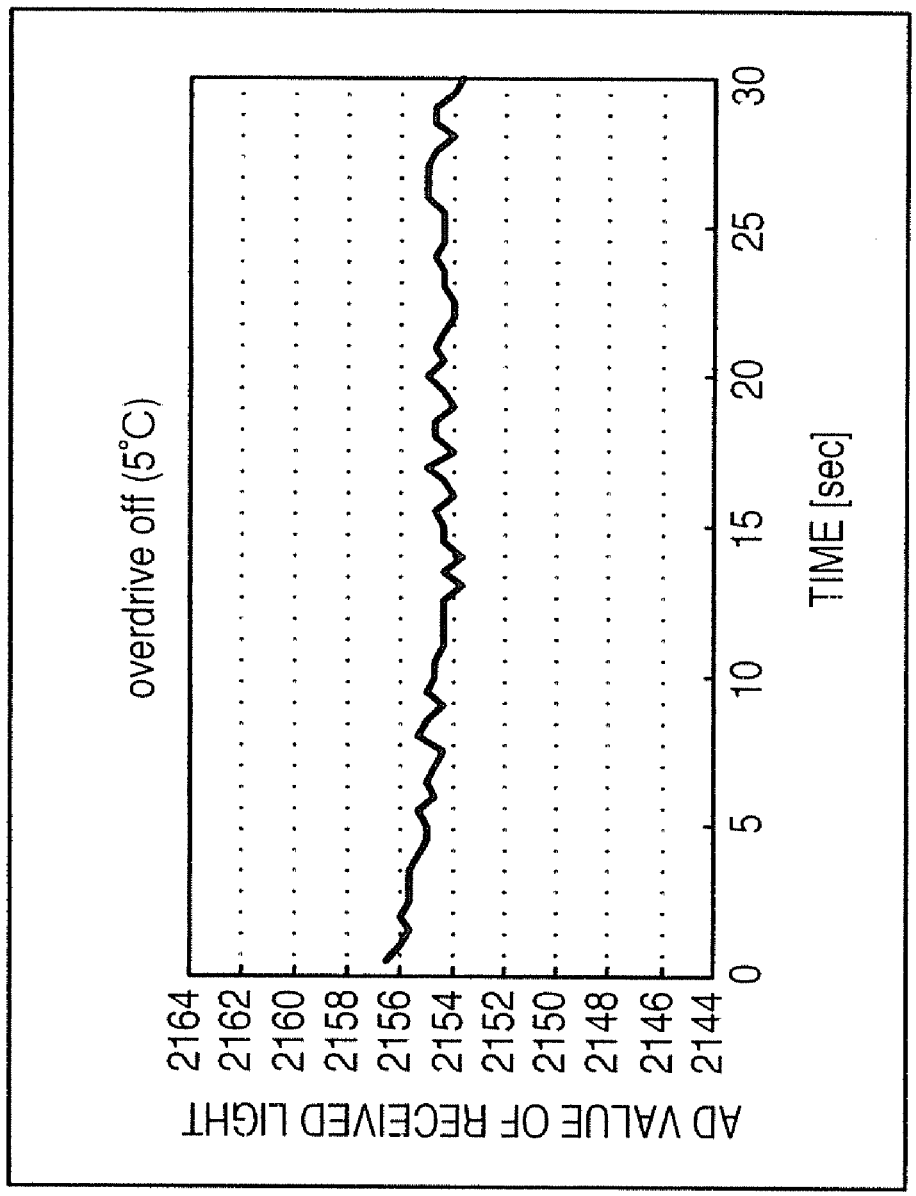
FIGS. 20A and 20B show the measurement results of the received light intensity according to the third embodiment.
Figure 20B:
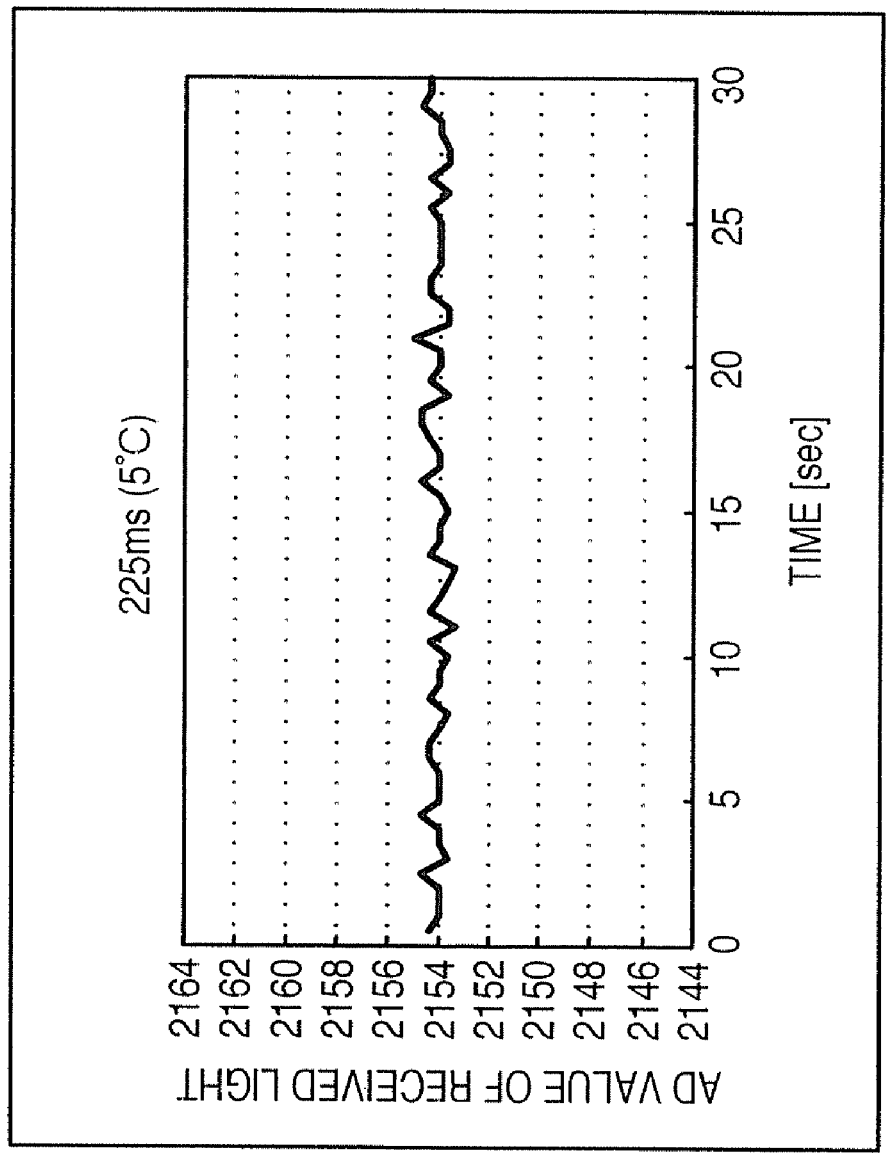

FIG. 20A shows the measurement result of the received light intensity at an ambient temperature of 5° C. when no light intensity stabilization processing was performed and the light-emitting element 114 was driven with 15 mA. FIG. 20B shows the measurement result of the received light intensity at an ambient temperature of 5° C. when light intensity stabilization processing was performed with continuous driving time of 225 msec, and the light-emitting element 114 was driven with 15 mA. Also in this case, it can be understood that the received light intensity is stabilized when light intensity stabilization processing was performed in contrast to when no light intensity stabilization processing was performed.

Further, as can be understood from FIGS. 18A, 19A and 20A, the lower the ambient temperature is, the better the received light intensity AD value stabilizes. Based on this, the present embodiment is set to use shorter continuous driving time of the light-emitting element 114 during light intensity stabilization processing according to lower ambient temperatures. With this, when measuring constituents of body fluid, it is possible to perform the light intensity stabilization processing which is appropriate for the measured ambient temperature. Note that in the present embodiment, a table, in which the correspondence of ambient temperature and the continuous driving time of the light-emitting element 114 during the light intensity stabilization processing is provided, is pre-stored in the memory 105. In this case, at S502 of FIG. 5, the CPU 101 (determination unit 109) obtains the continuous driving time corresponding to the measured ambient temperature from the memory 105, and determines conditions of light emission for light intensity stabilization processing.

Next, with reference to FIG. 21, a table 2100 having the correspondence of the ambient temperature and the continuous driving time which drives the light-emitting element 114 during the light intensity stabilization processing will be explained. FIG. 21 shows the table 2100 in which the conditions for light emission for the light intensity stabilization processing according to the third embodiment is registered.

The table 2100 which relates ambient temperatures 2101 to their corresponding continuous driving times 2102 of the driving pulse which drives the light-emitting element 114. The ambient temperatures 2101 are divided and defined in several segments, such as below 5.0° C., 5.1° C. to 10.0° C., . . . 30.1° C. to 35.0° C., and above 35.1° C. Further, the continuous driving time 2102 is set for each individual segment of temperature. The CPU 101 obtains the continuous driving time 2102 corresponding to the measured ambient temperature from the table 2100 as the condition of light emission of the light-emitting element 114 during the light intensity stabilization processing. In this particular example, the ambient temperature was divided into 5° C. segments. However, this example does not limit the present invention to use of 5° C. segments only, and it is preferable to adjust the segment range according to, for example, the accuracy of the device element and the capacity of the memory 105.

As explained above, the body fluid constituents measurement device 100 of the present embodiment alters the continuous driving time which drives the light-emitting element 114 during the light intensity stabilization processing in accordance with the ambient temperature. Due to this, the light intensity stabilization processing of the present embodiment can stabilize the light intensity emitted from the light-emitting element 114 in a short time after being switched on, while at the same time preparing to obtain accurate measurement results of the body fluid constituent. Further, when the ambient temperature in the vicinity of the light-emitting element 114 is low, it may suppress power consumption by reducing driving time of the light-emitting element 114.

Further, according to the present embodiment, the total sum of the light emitting time of the light-emitting element 114 during light intensity stabilization processing is 0.2 to 0.3 seconds. This value is considered about the differences that exist in LEDs manufactured by various manufacturers which are to be employed as the light-emitting element 114. Further, the continuous driving time for the light-emitting element 114 during the light intensity stabilization processing is preferably between 220 msec and 260 msec.

The present invention is not limited to the above embodiments, and can be changed or modified to various forms within the original intent and scope of the present invention. Accordingly, we provide following claims in order to publicize the scope of the present invention.

The invention claimed is:

1. A body fluid constituents measurement device which utilizes a test paper holding a coloring reagent which reacts to a predetermined constituent of body fluid, and optically measures a quantity of the predetermined constituent in the body fluid specimen by means of colorimetry, the body fluid constituents measurement device comprising:
   a light-emitting element configured to emit irradiating light to said test paper,
   a light-receiving element configured to receive reflected light from said test paper,
   a driving control unit configured to control driving of said light-emitting element,
   a temperature measurement unit configured to measure ambient temperature in the vicinity of said light-emitting element, and
   a determination unit configured to determine a first light emission condition for driving said light-emitting element prior to performing measurement of a quantity of the predetermined constituent based on the ambient temperature measured by said temperature measurement unit,
   wherein after said light-emitting element is driven for a predetermined period of time under said first light emission condition, the body fluid is provided to said test paper under a second light emission condition different from the first light emission condition, and the measurement of the quantity of the predetermined constituent of the body fluid is performed by detecting at said light-receiving element a reflected light intensity from the test paper where color change occurs according to the quantity of the predetermined constituent of the body fluid.

2. The body fluid constituents measurement device according to claim 1, further comprising a memory unit configured to store the information of said first light emission condition correlated with said ambient temperature, wherein said determination unit performs said determination by selecting said first light emission condition which corresponds to said ambient temperature from said first light emission conditions stored in said memory unit.

3. The body fluid constituents measurement device according to claim 1, wherein the pulse width of the control signal for controlling light emission of said light-emitting element in said first light emission condition is defined to be bigger than the pulse width in said second light emission condition.

4. The body fluid constituents measurement device according to claim 1, wherein the pulse amplitude of the control signal for controlling light emission of said light-emitting element in said first light emission condition is defined to be bigger than the pulse amplitude in said second light emission condition.

5. The body fluid constituents measurement device according to claim 1, wherein the pulse period of the control signal for controlling light emission of said light-emitting element in said first light emission condition is defined to be shorter than the pulse period in said second light emission condition.

6. The body fluid constituents measurement device according to claim 1, wherein said determination unit determines said predetermined period of time for driving of said light-emitting element based on said ambient temperature as said first light emission condition.

7. The body fluid constituents measurement device according to claim 6, wherein said predetermined period of time is the time from switching on said body fluid constituents measurement device to stabilization of light intensity emitted by said light-emitting element.

8. The body fluid constituents measurement device according to claim 7 wherein said predetermined period of time is between 0.2 to 2 seconds.

9. The body fluid constituents measurement device according to claim 1, wherein said determination unit determines duty ratio of the pulses for driving of said light-emitting element based on said ambient temperature as said first light emission condition.

10. The body fluid constituents measurement device according to claim 1, wherein said determination unit determines to continuously drive said light emitting element and also determines the ON period of the pulse of the continuous driving based on said ambient temperature as said first light emission condition.

11. A method of controlling a body fluid constituents measurement device which utilizes a test paper holding a coloring reagent which reacts to a predetermined constituent of body fluid, and optically measures a quantity of the predetermined constituent, the method comprising:

a temperature measuring step of measuring the ambient temperature in the vicinity of a light-emitting element, a determination step of determining a first light emission condition for driving said light-emitting element prior to performing measurement of a quantity of the predetermined constituent based on the measured ambient temperature, a first driving step of driving said light-emitting element for a predetermined period of time under said first light emission condition, and a second driving step of driving said light-emitting element under a second light emission condition different from said first light emission condition, wherein in said second driving step, the body fluid is provided to said test paper, and the measurement of the quantity of the predetermined constituent of the body fluid is performed by detecting at the light receiving element the reflected light intensity from the test paper, which is irradiated by the light emitted from said light emitting element.

12. The control method according to claim 11 wherein said determination step determines said predetermined period of time which drives said light-emitting element based on said ambient temperature as said first light emission condition.

13. The control method according to claim 12 wherein said predetermined period of time is the time from switching on said body fluid constituents measurement device to stabilization of light intensity emitted by said light-emitting element.

14. The control method according to claim 13 wherein said predetermined period of time is between 0.2 to 2 seconds.

15. The control method according to claim 11 wherein said determination step determines duty ratio of the pulses for driving of said light-emitting element based on said ambient temperature as said first light emission condition.

16. The control method according to claim 11 wherein said determination step determines to continuously drive said light-emitting element, and also determines the ON period of the pulse of the continuous driving based on said ambient temperature as said first light emission condition.

* * * * *